United States Patent [19]

Connors

[11] Patent Number: 5,218,090
[45] Date of Patent: Jun. 8, 1993

[54] EGF RECEPTOR TRUNCATES

[75] Inventor: Richard W. Connors, Saline, Mich.

[73] Assignee: Warner-Lambert Company, Morris Plains, N.J.

[21] Appl. No.: 604,728

[22] Filed: Oct. 26, 1990

Related U.S. Application Data

[63] Continuation-in-part of Ser. No. 536,896, Jun. 12, 1990, abandoned.

[51] Int. Cl.$^5$ .................... C07K 13/00; C12N 15/12
[52] U.S. Cl. ................... 530/350; 435/69.1; 435/252.3; 536/23.5
[58] Field of Search .................. 530/350; 536/27; 435/252.3

[56] References Cited

U.S. PATENT DOCUMENTS

| | | | |
|---|---|---|---|
| 4,745,051 | 5/1988 | Smith et al. | 435/69.1 |
| 4,859,609 | 8/1989 | Dull et al. | 436/501 |
| 4,879,236 | 11/1989 | Smith et al. | 435/235 |
| 4,933,294 | 6/1990 | Waterfield et al. | 436/501 |

OTHER PUBLICATIONS

Science 224, 294-14 297, 20 Apr. 1984, Weber et al., Production of an Epidermal Growth Factor Receptor-Related Protein.
J. Cell. Brichem. 34:239-245, 1987, Marsh et al., Vaccinia Virus and the EGF Receptor: A Portal for Infectivity?.
Mol & Cell. Biol. 8:1831-1834, Apr. 1988, Lax et al. Localization of a Major Receptor-Binding Domain for Epidermal Growth Factor by Affinity Labeling.
Science 238: 1704-1707, 18 Dec. 1987, Smith et al., Blocking of HIV-1 Infectivity by a Soluble, Secreted Form of the CDU Antigen.
Ullrich, A. et al., "Human Epidermal Growth . . . ", Nature, vol. 309, pp. 418-425, (31 May 1984).
Prywes, R., et al., "Mutations in the Cytoplasmic . . . ", Embo Journal, vol. 5, No. 9, pp. 2179-2190 (Sep. '86).
Todaro, G. J., et al., "Transforming Growth Factors . . . ", Proc. Natl. Acad. Sci USA, vol. 77, No. 9, pp. 5258-5262 (Sep. 1980).
Shoyab, M., et al., "Structure and Function of Human . . . ", Science, vol. 243, pp. 1074-1076 (Feb. 24, 1989).
Stroobant, P., et al., "Purification and Characterization . . . ", Cell, vol. 42, pp. 383-393 (Aug. 1985).
Gullick, W. J., et al., "The Structure and Function . . . ", Proc. R. Soc. Lond. B., pp. 127-134 (Oct. 22, 1985).
Lax, I., et al., "Localization of a Major Receptor-. . . ", Mol. Cell. Biol., vol. 8, No. 4, pp. 1831-1834 (Apr. 1988).
Greenfield, C., et al., "Epidermal Growth Factor . . . ", Embo Journal, vol. 8, No. 13, pp. 4115-4123 (Aug. 1989).
Toneguzzo, F., et al., "Electric Field-Mediated DNA . . . ", Mol. Cell. Biol., vol. 6, No. 2, pp. 703-706 (1986).
Gluzman, Yakov, "SV40-Transformed Simian Cells . . . ", Cell, vol. 23, pp. 175-182, (Jan. 1981).
Wigler, M., et al., "Transformation of Mammalian Cells . . . ", Proc. Natl. Acad. Sci. USA, vol. 77, No. 6, pp. 3567-3570 (Jun. 1980).
Marsh, Y. V., et al., "Vaccinia Virus and the EGF . . . ", Jour. of Cellular Biochemistry, vol. 34, pp. 239-245 (Apr. 1986).
Eppstein, D. A., et al. "Epidermal Growth Factor . . . ", Nature, vol. 318, pp. 663-665 (Dec. 1985).

Primary Examiner—Robert J. Hill, Jr.
Assistant Examiner—John D. Ulm
Attorney, Agent, or Firm—Ronald A. Daignault

[57] ABSTRACT

The present invention is for EGF receptor truncates which retain the activity of ligand binding for the EGF receptor. The specific truncates include $LD_1D_2D_3$.ApaL encompassing amino acids $Met_{-24}$ to $Val_{505}$ of the EGF receptor; for $LD_2D_3D_4$ which melds the EGF receptor leader peptide (amino acids $Met_{-24}$ to $Ala_{-1}$), 9 amino acids of the mature amino terminus of the receptor ($Leu_1$ to $Gly_9$) and receptor sequences $Ser_{150}$ to $Gly_{625}$; for $LD_3D_4$ which is the leader peptide ($Met_{-24}$ to $Ala_{-1}$), $Leu_1$ to $Gln_8$ of the mature amino terminus and the receptor sequence $Asp_{297}$ to $Gly_{625}$.

4 Claims, 37 Drawing Sheets

BglII

```
  1 GACGGATCGGGAGATCTCCCGATCCCCTATGGTGCACTCTCAGTA
    CTGCCTAGCCCTCTAGAGGGCTAGGGGATACCACGTGAGAGTCAT
 46 CAATCTGCTCTGATGCCGCATAGTTAAGCCAGTATCTGCTCCCTG
    GTTAGACGAGACTACGGCGTATCAATTCGGTCATAGACGAGGGAC
 91 CTTGTGTGTTGGAGGTCGCTGAGTAGTGCGCGAGCAAAATTTAAG
    GAACACACAACCTCCAGCGACTCATCACGCGCTCGTTTTAAATTC
136 CTACAACAAGGCAAGGCTTGACCGACAATTGCATGAAGAATCTGC
    GATGTTGTTCCGTTCCGAACTGGCTGTTAACGTACTTCTTAGACG
181 TTAGGGTTAGGCGTTTTGCGCTGCTTCGCGATGTACGGGCCAGAT
    AATCCCAATCCGCAAAACGCGACGAAGCGCTACATGCCCGGTCTA
```
MluI
AflIII
```
226 ATACGCGTATCTGAGGGGACTAGGGTGTGTTTAGGCGAAAAGCGG
    TATGCGCATAGACTCCCCTGATCCCACACAAATCCGCTTTTCGCC
271 GGCTTCGGTTGTACGCGGTTAGGAGTCCCCTCAGGATATAGTAGT
    CCGAAGCCAACATGCGCCAATCCTCAGGGGAGTCCTATATCATCA
316 TTCGCTTTTGCATAGGGAGGGGGAAATGTAGTCTTATGCAATACA
    AAGCGAAAACGTATCCCTCCCCCTTTACATCAGAATACGTTATGT
361 CTTGTAGTCTTGCAACATGGTAACGATGAGTTAGCAACATGCCTT
    GAACATCAGAACGTTGTACCATTGCTACTCAATCGTTGTACGGAA
406 ACAAGGAGAGAAAAAGCACCGTGCATGCCGATTGGTGGAAGTAAG
    TGTTCCTCTCTTTTTCGTGGCACGTACGGCTAACCACCTTCATTC
451 GTGGTACGATCGTGCCTTATTAGGAAGGCAACAGACAGGTCTGAC
    CACCATGCTAGCACGGAATAATCCTTCCGTTGTCTGTCCAGACTG
496 ATGGATTGGACGAACCACTGAATTCCGCATTGCAGAGATAATTGT
    TACCTAACCTGCTTGGTGACTTAAGGCGTAACGTCTCTATTAACA
541 ATTTAAGTGCCTAGCTCGATACAATAAACGCCATTTGACCATTCA
    TAAATTCACGGATCGAGCTATGTTATTTGCGGTAAACTGGTAAGT
```
HindIII
```
586 CCACATTGGTGTGCACCTCCAAGCTTGGGCTGCAGGTCGACTCTA
    GGTGTAACCACACGTGGAGGTTCGAACCCGACGTCCAGCTGAGAT
```
BamHI                                          START D1D2D3.APA  L
```
631 GAGGATCCCCGGGCGAGCTCTTCGGGGAGCAGCGATGCGACCCTC
    CTCCTAGGGGCCCGCTCGAGAAGCCCCTCGTCGCTACGCTGGGAG
```

FIGURE 3A

```
 676 CGGGA CGGCCGGGGCAGCGCT CCTGGCGCTGCGGCTGCGCTCTGC
     GCCCTGCCGGCCCCGTCGCGAGGACCGCGACGCCGACGCGAGACG
                                              StyI
 721 CCGGCGAGTCGGGCTCTGGAGGAAAAGAAAGTTTGCCAAGGCACG
     GGCCGCTCAGCCCGAGACCTCCTTTTCTTTCAAACGGTTCCGTGC
 766 AGTAACAAGCTCACGCAGTTGGGCACTTTTGAAGATCATTTTCTC
     TCATTGTTCGAGTGCGTCAACCCGTGAAAACTTCTAGTAAAAGAG
                                              StyI
 811 AGCCTCCAGAGGATGTTCAATAACTGTGAGGTGGTCCTTGGGAAT
     TCGGAGGTCTCCTACAAGTTATTGACACTCCACCAGGAACCCTTA
 856 TTGGAAATTACCTATGTGCAGAGGAATTATGATCTTTCCTTCTTA
     AACCTTTAATGGATACACGTCTCCTTAATACTAGAAAGGAAGAAT
 901 AAGACCATCCAGGAGGTGGCTGGTTATGTCCTCATTGCCCTCAAC
     TTCTGGTAGGTCCTCCACCGACCAATACAGGAGTAACGGGAGTTG
 946 ACAGTGGAGCGAATTCCTTTGGAAAACCTGCAGATCATCAGAGGA
     TGTCACCTCGCTTAAGGAAACCTTTTGGACGTCTAGTAGTCTCCT
 991 AATATGTACTACGAAAATTCCTATGCCTTAGCAGTCTTATCTAAC
     TTATACATGATGCTTTTAAGGATACGGAATCGTCAGAATAGATTG
1036 TATGATGCAAATAAAACCGGACTGAAGGAGCTGCCCATGAGAAAT
     ATACTACGTTTATTTTGGCCTGACTTCCTCGACGGGTACTCTTTA
1081 TTACAGGAAATCCTGCATGGCGCCGTGCGGTTCAGCAACAACCCT
     AATGTCCTTTAGGACGTACCGCGGCACGCCAAGTCGTTGTTGGGA
1126 GCCCTGTGCAACGTGGAGAGCATCCAGTGGCGGGACATAGTCAGC
     CGGGACACGTTGCACCTCTCGTAGGTCACCGCCCTGTATCAGTCG
                                           AflIII
1171 AGTGACTTTCTCAGCAACATGTCGATGGACTTCCAGAACCACCTG
     TCACTGAAAGAGTCGTTGTACAGCTACCTGAAGGTCTTGGTGGAC
1216 GGCAGCTGCCAAAAGTGTGATCCAAGCTGTCCCAATGGGAGCTGC
     CCGTCGACGGTTTTCACACTAGGTTCGACAGGGTTACCCTCGACG
1261 TGGGGTGCAGGAGAGGAGAACTGCCAGAAACTGACCAAAATCATC
     ACCCCACGTCCTCTCCTCTTGACGGTCTTTGACTGGTTTTAGTAG
1306 TGTGCCCAGCAGTGCTCCGGGCGCTGCCGTGGCAAGTCCCCCAGT
     ACACGGGTCGTCACGAGGCCCGCGACGGCACCGTTCAGGGGGTCA
1351 GACTGCTGCCACAACCAGTGTGCTGCAGGCTGCACAGGCCCCCGG
     CTGACGACGGTGTTGGTCACACGACGTCCGACGTGTCCGGGGGCC
```

FIGURE 3B

```
1396 GAGAGCGACTGCCTGGTCTGCCGCAAATTCCGAGACGAAGCCACG
     CTCTCGCTGACGGACCAGACGGCGTTTAAGGCTCTGCTTCGGTGC
1441 TGCAAGGACACCTGCCCCCCACTCATGCTCTACAACCCCACCACG
     ACGTTCCTGTGGACGGGGGGTGAGTACGAGATGTTGGGGTGGTGC
1486 TACCAGATGGATGTGAACCCCGAGGGCAAATACAGCTTTGGTGCC
     ATGGTCTACCTACACTTGGGGCTCCCGTTTATGTCGAAACCACGG
1531 ACCTGCGTGAAGAAGTGTCCCCGTAATTATGTGGTGACAGATCAC
     TGGACGCACTTCTTCACAGGGGCATTAATACACCACTGTCTAGTG
1576 GGCTCGTGCGTCCGAGCCTGTGGGGCCGACAGCTATGAGATGGAG
     CCGAGCACGCAGGCTCGGACACCCCGGCTGTCGATACTCTACCTC
1621 GAAGACGGCGTCCGCAAGTGTAAGAAGTGCGAAGGGCCTTGCCGC
     CTTCTGCCGCAGGCGTTCACATTCTTCACGCTTCCCGGAACGGCG
1666 AAAGTGTGTAACGGAATAGGTATTGGTGAATTTAAAGACTCACTC
     TTTCACACATTGCCTTATCCATAACCACTTAAATTTCTGAGTGAG
1711 TCCATAAATGCTACGAATATTAAACACTTCAAAAACTGCACCTCC
     AGGTATTTACGATGCTTATAATTTGTGAAGTTTTTGACGTGGAGG
1756 ATCAGTGGCGATCTCCACATCCTGCCGGTGGCATTTAGGGGTGAC
     TAGTCACCGCTAGAGGTGTAGGACGGCCACCGTAAATCCCCACTG
                                 BamHI
1801 TCCTTCACACATACTCCTCCTCTGGATCCACAGGAACTGGATATT
     AGGAAGTGTGTATGAGGAGGAGACCTAGGTGTCCTTGACCTATAA
1846 CTGAAAACCGTAAAGGAAATCACAGGGTTTTTGCTGATTCAGGCT
     GACTTTTGGCATTTCCTTTAGTGTCCCAAAAACGACTAAGTCCGA
1891 TGGCCTGAAAACAGGACGGACCTCCATGCCTTTGAGAACCTAGAA
     ACCGGACTTTTGTCCTGCCTGGAGGTACGGAAACTCTTGGATCTT
1936 ATCARACGCGGCAGGACCAAGCAACATGGTCAGTTTTCTCTTGCA
     TAGTYTGCGCCGTCCTGGTTCGTTGTACCAGTCAAAAGAGAACGT
              Styl
1981 GTCGTCAGCCTGAACATAACATCCTTGGGATTACGCTCCCTCAAG
     CAGCAGTCGGACTTGTATTGTAGGAACCCTAATGCGAGGGAGTTC
2026 GAGATAAGTGATGGAGATGTGATAATTTCAGGAAACAAAAATTTG
     CTCTATTCACTACCTCTACACTATTAAAGTCCTTTGTTTTTAAAC
2071 TGCTATGCAAATACAATAAACTGGAAAAAACTGTTTGGGACCTCC
     ACGATACGTTTATGTTATTTGACCTTTTTTGACAAACCCTGGAGG
```

FIGURE 3C

```
2116 GGTCAGAAAACCAAAATTATAAGCAACAGAGGTGAAAACAGCTGC
     CCAGTCTTTTGGTTTTAATATTCGTTGTCTCCACTTTTGTCGACG
2161 AAGGCCACAGGCCAGGTCTGCCATGCCTTGTGCTCCCCCGAGGGC
     TTCCGGTGTCCGGTCCAGACGGTACGGAACACGAGGGGGCTCCCG
              ApaI
2206 TGCTGGGGCCCCGAGCCCAGGGACTGCGTCTCTTGCCGGAATGTC
     ACGACCCCGGGGCTCGGGTCCCTGACGCAGAGAACGGCCTTACAG
     D1D2D3.APA L STOP
                  BstXI
2251 TGATAAGCTTCCAGCACAATGGATCTCGAGGTCGAGGGATCTCTA
     ACTATTCGAAGGTCGTGTTACCTAGAGCTCCAGCTCCCTAGAGAT
2296 GAGCTCGCTGATCAGCCTCGACTGTGCCTTCTAGTTGCCAGCCAT
     CTCGAGCGACTAGTCGGAGCTGACACGGAAGATCAACGGTCGGTA
2341 CTGTTGTTTGCCCCTCCCCCGTGCCTTCCTTGACCCTGGAAGGTG
     GACAACAAACGGGGAGGGGGCACGGAAGGAACTGGGACCTTCCAC
2386 CCACTCCCACTGTCCTTTCCTAATAAAATGAGGAAATTGCATCGC
     GGTGAGGGTGACAGGAAAGGATTATTTTACTCCTTTAACGTAGCG
2431 ATTGTCTGAGTAGGTGTCATTCTATTCTGGGGGGTGGGGTGGGGC
     TAACAGACTCATCCACAGTAAGATAAGACCCCCCACCCCACCCCG
2476 AGGACAGCAAGGGGGAGGATTGGGAAGACAATAGCAGGCATGCTG
     TCCTGTCGTTCCCCCTCCTAACCCTTCTGTTATCGTCCGTACGAC
                                          BamHI
2521 GGGATGCGGTGGGCTCTATGGAACCAGCTGGGGCTCGAGGGGGGA
     CCCTACGCCACCCGAGATACCTTGGTCGACCCCGAGCTCCCCCCT
         EcoRI
2566 TCCCCGGGAATTCTGTGGAATGTGTGTCAGTTAGGGTGTGGAAAG
     AGGGGCCCTTAAGACACCTTACACACAGTCAATCCCACACCTTTC
2611 TCCCCAGGCTCCCCAGCAGGCAGAAGTATGCAAAGCATGCATCTC
     AGGGGTCCGAGGGGTCGTCCGTCTTCATACGTTTCGTACGTAGAG
2656 AATTAGTCAGCAACCAGGTGTGGAAAGTCCCCAGGCTCCCCAGCA
     TTAATCAGTCGTTGGTCCACACCTTTCAGGGGTCCGAGGGGTCGT
2701 GGCAGAAGTATGCAAAGCATGCATCTCAATTAGTCAGCAACCATA
     CCGTCTTCATACGTTTCGTACGTAGAGTTAATCAGTCGTTGGTAT
2746 GTCCCGCCCCTAACTCCGCCCATCCCGCCCCTAACTCCGCCCAGT
     CAGGGCGGGGATTGAGGCGGGTAGGGCGGGGATTGAGGCGGGTCA
```

FIGURE 3D

StyI

```
2791 TCCGCCCATTCTCCGCCCCATGGCTGACTAATTTTTTTATTTAT
     AGGCGGGTAAGAGGCGGGGTACCGACTGATTAAAAAAATAAATA
2836 GCAGAGGCCGAGGCCGCCTCGGCCTCTGAGCTATTCCAGAAGTAG
     CGTCTCCGGCTCCGGCGGAGCCGGAGACTCGATAAGGTCTTCATC
```

StyI

```
2881 TGAGGAGGCTTTTTTGGAGGCCTAGGCTTTTGCAAAAAGCTCCCG
     ACTCCTCCGAAAAAACCTCCGGATCCGAAAACGTTTTCGAGGGC
2926 GGAGCTTGGATATCCATTTTCGGATCTGATCAAGAGACAGGATGA
     CCTCGAACCTATAGGTAAAAGCCTAGACTAGTTCTCTGTCCTACT
2971 GGATCGTTTCGCATGATTGAACAAGATGGATTGCACGCAGGTTCT
     CCTAGCAAAGCGTACTAACTTGTTCTACCTAACGTGCGTCCAAGA
3016 CCGGCCGCTTGGGTGGAGAGGCTATTCGGCTATGACTGGGCACAA
     GGCCGGCGAACCCACCTCTCCGATAAGCCGATACTGACCCGTGTT
3061 CAGACAATCGGCTGCTCTGATGCCGCCGTGTTCCGGCTGTCAGCG
     GTCTGTTAGCCGACGAGACTACGGCGGCACAAGGCCGACAGTCGC
3106 CAGGGGCGCCCGGTTCTTTTTGTCAAGACCGACCTGTCCGGTGCC
     GTCCCCGCGGGCCAAGAAAACAGTTCTGGCTGGACAGGCCACGG
3151 CTGAATGAACTGCAGGACGAGGCAGCGCGGCTATCGTGGCTGGCC
     GACTTACTTGACGTCCTGCTCCGTCGCGCCGATAGCACCGACCGG
3196 ACGACGGGCGTTCCTTGCGCAGCTGTGCTCGACGTTGTCACTGAA
     TGCTGCCCGCAAGGAACGCGTCGACACGAGCTGCAACAGTGACTT
3241 GCGGGAAGGGACTGGCTGCTATTGGGCGAAGTGCCGGGGCAGGAT
     CGCCCTTCCCTGACCGACGATAACCCGCTTCACGGCCCCGTCCTA
3286 CTCCTGTCATCTCACCTTGCTCCTGCCGAGAAAGTATCCATCATG
     GAGGACAGTAGAGTGGAACGAGGACGGCTCTTTCATAGGTAGTAC
3331 GCTGATGCAATGCGGCGGCTGCATACGCTTGATCCGGCTACCTGC
     CGACTACGTTACGCCGCCGACGTATGCGAACTAGGCCGATGGACG
3376 CCATTCGACCACCAAGCGAAACATCGCATCGAGCGAGCACGTACT
     GGTAAGCTGGTGGTTCGCTTTGTAGCGTAGCTCGCTCGTGCATGA
3421 CGGATGGAAGCCGGTCTTGTCGATCAGGATGATCTGGACGAAGAG
     GCCTACCTTCGGCCAGAACAGCTAGTCCTACTAGACCTGCTTCTC
3466 CATCAGGGGCTCGCGCCAGCCGAACTGTTCGCCAGGCTCAAGGCG
     GTAGTCCCCGAGCGCGGTCGGCTTGACAAGCGGTCCGAGTTCCGC
```

FIGURE 3E

```
                                                                StyI
3511 CGCATGCCCGACGGCGAGGATCTCGTCGTGACCCATGGCGATGCC
     GCGTACGGGCTGCCGCTCCTAGAGCAGCACTGGGTACCGCTACGG
3556 TGCTTGCCGAATATCATGGTGGAAAATGGCCGCTTTTCTGGATTC
     ACGAACGGCTTATAGTACCACCTTTTACCGGCGAAAAGACCTAAG
3601 ATCGACTGTGGCCGGCTGGGTGTGGCGGACCGCTATCAGGACATA
     TAGCTGACACCGGCCGACCCACACCGCCTGGCGATAGTCCTGTAT
3646 GCGTTGGCTACCCGTGATATTGCTGAAGAGCTTGGCGGCGAATGG
     CGCAACCGATGGGCACTATAACGACTTCTCGAACCGCCGCTTACC
3691 GCTGACCGCTTCCTCGTGCTTTACGGTATCGCCGCTCCCGATTCG
     CGACTGGCGAAGGAGCACGAAATGCCATAGCGGCGAGGGCTAAGC
3736 CAGCGCATCGCCTTCTATCGCCTTCTTGACGAGTTCTTCTGAGCG
     GTCGCGTAGCGGAAGATAGCGGAAGAACTGCTCAAGAAGACTCGC
3781 GGACTCTGGGGTTCGAAATGACCGACCAAGCGACGCCCAACCTGC
     CCTGAGACCCCAAGCTTTACTGGCTGGTTCGCTGCGGGTTGGACG
3826 CATCACGAGATTTCGATTCCACCGCCGCCTTCTATGAAAGGTTGG
     GTAGTGCTCTAAAGCTAAGGTGGCGGCGGAAGATACTTTCCAACC
3871 GCTTCGGAATCGTTTTCCGGGACGCCGGCTGGATGATCCTCCAGC
     CGAAGCCTTAGCAAAAGGCCCTGCGGCCGACCTACTAGGAGGTCG
3916 GCGGGGATCTCATGCTGGAGTTCTTCGCCCACCCCAACTTGTTTA
     CGCCCCTAGAGTACGACCTCAAGAAGCGGGTGGGGTTGAACAAAT
3961 TTGCAGCTTATAATGGTTACAAATAAAGCAATAGCATCACAAATT
     AACGTCGAATATTACCAATGTTTATTTCGTTATCGTAGTGTTTAA
4006 TCACAAATAAAGCATTTTTTCACTGCATTCTAGTTGTGGTTTGT
     AGTGTTTATTTCGTAAAAAAGTGACGTAAGATCAACACCAAACA
                                                                BamHI
4051 CCAAACTCATCAATGTATCTTATCATGTCTGGATCCCGTCGACCT
     GGTTTGAGTAGTTACATAGAATAGTACAGACCTAGGGCAGCTGGA
4096 CGAGAGCTTGGCGTAATCATGGTCATAGCTGTTTCCTGTGTGAAA
     GCTCTCGAACCGCATTAGTACCAGTATCGACAAAGGACACACTTT
4141 TTGTTATCCGCTCACAATTCCACACAACATACGAGCCGGAAGCAT
     AACAATAGGCGAGTGTTAAGGTGTGTTGTATGCTCGGCCTTCGTA
4186 AAAGTGTAAAGCCTGGGGTGCCTAATGAGTGAGCTAACTCACATT
     TTTCACATTTCGGACCCCACGGATTACTCACTCGATTGAGTGTAA
```

FIGURE 3F

```
4231 AATTGCGTTGCGCTCACTGCCCGCTTTCCAGTCGGGAAACCTGTC
     TTAACGCAACGCGAGTGACGGGCGAAAGGTCAGCCCTTTGGACAG
4276 GTGCCAGCTGCATTAATGAATCGGCCAACGCGCGGGGAGAGGCGG
     CACGGTCGACGTAATTACTTAGCCGGTTGCGCGCCCCTCTCCGCC
4321 TTTGCGTATTGGGCGCTCTTCCGCTTCCTCGCTCACTGACTCGCT
     AAACGCATAACCCGCGAGAAGGCGAAGGAGCGAGTGACTGAGCGA
4366 GCGCTCGGTCGTTCGGCTGCGGCGAGCGGTATCAGCTCACTCAAA
     CGCGAGCCAGCAAGCCGACGCCGCTCGCCATAGTCGAGTGAGTTT
4411 GGCGGTAATACGGTTATCCACAGAATCAGGGGATAACGCAGGAAA
     CCGCCATTATGCCAATAGGTGTCTTAGTCCCCTATTGCGTCCTTT
                AflIII
4456 GAACATGTGAGCAAAAGGCCAGCAAAAGGCCAGGAACCGTAAAAA
     CTTGTACACTCGTTTTCCGGTCGTTTTCCGGTCCTTGGCATTTTT
4501 GGCCGCGTTGCTGGCGTTTTTCCATAGGCTCCGCCCCCCTGACGA
     CCGGCGCAACGACCGCAAAAAGGTATCCGAGGCGGGGGGACTGCT
4546 GCATCACAAAAATCGACGCTCAAGTCAGAGGTGGCGAAACCCGAC
     CGTAGTGTTTTTAGCTGCGAGTTCAGTCTCCACCGCTTTGGGCTG
4591 AGGACTATAAAGATACCAGGCGTTTCCCCCTGGAAGCTCCCTCGT
     TCCTGATATTTCTATGGTCCGCAAAGGGGGACCTTCGAGGGAGCA
4636 GCGCTCTCCTGTTCCGACCCTGCCGCTTACCGGATACCTGTCCGC
     CGCGAGAGGACAAGGCTGGGACGGCGAATGGCCTATGGACAGGCG
4681 CTTTCTCCCTTCGGGAAGCGTGGCGCTTTCTCAATGCTCACGCTG
     GAAAGAGGGAAGCCCTTCGCACCGCGAAAGAGTTACGAGTGCGAC
4726 TAGGTATCTCAGTTCGGTGTAGGTCGTTCGCTCCAAGCTGGGCTG
     ATCCATAGAGTCAAGCCACATCCAGCAAGCGAGGTTCGACCCGAC
4771 TGTGCACGAACCCCCCGTTCAGCCCGACCGCTGCGCCTTATCCGG
     ACACGTGCTTGGGGGGCAAGTCGGGCTGGCGACGCGGAATAGGCC
4816 TAACTATCGTCTTGAGTCCAACCCGGTAAGACACGACTTATCGCC
     ATTGATAGCAGAACTCAGGTTGGGCCATTCTGTGCTGAATAGCGG
4861 ACTGGCAGCAGCCACTGGTAACAGGATTAGCAGAGCGAGGTATGT
     TGACCGTCGTCGGTGACCATTGTCCTAATCGTCTCGCTCCATACA
4906 AGGCGGTGCTACAGAGTTCTTGAAGTGGTGGCCTAACTACGGCTA
     TCCGCCACGATGTCTCAAGAACTTCACCACCGGATTGATGCCGAT
4951 CACTAGAAGGACAGTATTTGGTATCTGCGCTCTGCTGAAGCCAGT
     GTGATCTTCCTGTCATAAACCATAGACGCGAGACGACTTCGGTCA
```

FIGURE 3G

```
4996  TACCTTCGGAAAAAGAGTTGGTAGCTCTTGATCCGGCAAACAAAC
      ATGGAAGCCTTTTTCTCAACCATCGAGAACTAGGCCGTTTGTTTG
5041  CACCGCTGGTAGCGGTGGTTTTTTTGTTTGCAAGCAGCAGATTAC
      GTGGCGACCATCGCCACCAAAAAAACAAACGTTCGTCGTCTAATG
5086  GCGCAGAAAAAAGGATCTCAAGAAGATCCTTTGATCTTTTCTAC
      CGCGTCTTTTTTTCCTAGAGTTCTTCTAGGAAACTAGAAAAGATG
5131  GGGGTCTGACGCTCAGTGGAACGAAAACTCACGTTAAGGGATTTT
      CCCCAGACTGCGAGTCACCTTGCTTTTGAGTGCAATTCCCTAAAA
5176  GGTCATGAGATTATCAAAAAGGATCTTCACCTAGATCCTTTTAAA
      CCAGTACTCTAATAGTTTTTCCTAGAAGTGGATCTAGGAAAATTT
5221  TTAAAAATGAAGTTTTAAATCAATCTAAAGTATATATGAGTAAAC
      AATTTTACTTCAAAATTTAGTTAGATTTCATATATACTCATTTG
5266  TTGGTCTGACAGTTACCAATGCTTAATCAGTGAGGCACCTATCTC
      AACCAGACTGTCAATGGTTACGAATTAGTCACTCCGTGGATAGAG
5311  AGCGATCTGTCTATTTCGTTCATCCATAGTTGCCTGACTCCCCGT
      TCGCTAGACAGATAAAGCAAGTAGGTATCAACGGACTGAGGGGCA
5356  CGTGTAGATAACTACGATACGGGAGGGCTTACCATCTGGCCCCAG
      GCACATCTATTGATGCTATGCCCTCCCGAATGGTAGACCGGGGTC
5401  TGCTGCAATGATACCGCGAGACCCACGCTCACCGGCTCCAGATTT
      ACGACGTTACTATGGCGCTCTGGGTGCGAGTGGCCGAGGTCTAAA
5446  ATCAGCAATAAACCAGCCAGCCGGAAGGGCCGAGCGCAGAAGTGG
      TAGTCGTTATTTGGTCGGTCGGCCTTCCCGGCTCGCGTCTTCACC
5491  TCCTGCAACTTTATCCGCCTCCATCCAGTCTATTAATTGTTGCCG
      AGGACGTTGAAATAGGCGGAGGTAGGTCAGATAATTAACAACGGC
5536  GGAAGCTAGAGTAAGTAGTTCGCCAGTTAATAGTTTGCGCAACGT
      CCTTCGATCTCATTCATCAAGCGGTCAATTATCAAACGCGTTGCA
5581  TGTTGCCATTGCTACAGGCATCGTGGTGTCACGCTCGTCGTTTGG
      ACAACGGTAACGATGTCCGTAGCACCACAGTGCGAGCAGCAAACC
5626  TATGGCTTCATTCAGCTCCGGTTCCCAACGATCAAGGCGAGTTAC
      ATACCGAAGTAAGTCGAGGCCAAGGGTTGCTAGTTCCGCTCAATG
5671  ATGATCCCCCATGTTGTGCAAAAAAGCGGTTAGCTCCTTCGGTCC
      TACTAGGGGGTACAACACGTTTTTTCGCCAATCGAGGAAGCCAGG
5716  TCCGATCGTTGTCAGAAGTAAGTTGGCCGCAGTGTTATCACTCAT
      AGGCTAGCAACAGTCTTCATTCAACCGGCGTCACAATAGTGAGTA
```

FIGURE 3H

```
5761 GGTTATGGCAGCACTGCATAATTCTCTTACTGTCATGCCATCCGT
     CCAATACCGTCGTGACGTATTAAGAGAATGACAGTACGGTAGGCA
5806 AAGATGCTTTCTGTGACTGGTGAGTACTCAACCAAGTCATTCTG
     TTCTACGAAAAGACACTGACCACTCATGAGTTGGTTCAGTAAGAC
5851 AGAATAGTGTATGCGGCGACCGAGTTGCTCTTGCCCGGCGTCAAT
     TCTTATCACATACGCCGCTGGCTCAACGAGAACGGGCCGCAGTTA
5896 ACGGGATAATACCGCGCCACATAGCAGAACTTTAAAAGTGCTCAT
     TGCCCTATTATGGCGCGGTGTATCGTCTTGAAATTTTCACGAGTA
5941 CATTGGAAAACGTTCTTCGGGGCGAAAACTCTCAAGGATCTTACC
     GTAACCTTTTGCAAGAAGCCCCGCTTTTGAGAGTTCCTAGAATGG
5986 GCTGTTGAGATCCAGTTCGATGTAACCCACTCGTGCACCCAACTG
     CGACAACTCTAGGTCAAGCTACATTGGGTGAGCACGTGGGTTGAC
6031 ATCTTCAGCATCTTTTACTTTCACCAGCGTTTCTGGGTGAGCAAA
     TAGAAGTCGTAGAAAATGAAAGTGGTCGCAAAGACCCACTCGTTT
6076 AACAGGAAGGCAAAATGCCGCAAAAAGGGAATAAGGGCGACACG
     TTGTCCTTCCGTTTTACGGCGTTTTTCCCTTATTCCCGCTGTGC
6121 GAAATGTTGAATACTCATACTCTTCCTTTTTCAATATTATTGAAG
     CTTTACAACTTATGAGTATGAGAAGGAAAAAGTTATAATAACTTC
6166 CATTTATCAGGGTTATTGTCTCATGAGCGGATACATATTTGAATG
     GTAAATAGTCCCAATAACAGAGTACTCGCCTATGTATAAACTTAC
6211 TATTTAGAAAAATAAACAAATAGGGGTTCCGCGCACATTTCCCCG
     ATAAATCTTTTATTTGTTTATCCCCAAGGCGCGTGTAAAGGGGC
6256 AAAAGTGCCACCTGACGTC
     TTTTCACGGTGGACTGCAG
```

FIGURE 3I

OPEN READING FRAME ANALYSIS

DNA> pRLD1D2D3.ApaL starts at nt #: +665
number of amino acids: 529
molecular weight: 58185

Three letter representation:
-24
met-arg-pro-ser-gly-thr-ala-gly-ala-ala-
leu-leu-ala-leu-leu-ala-ala-leu-cys-pro-
+1
ala-ser-arg-ala-leu-glu-glu-lys-lys-val-
cys-gln-gly-thr-ser-asn-lys-leu-thr-gln-
leu-gly-thr-phe-glu-asp-his-phe-leu-ser-
leu-gln-arg-met-phe-asn-asn-cys-glu-val-
val-leu-gly-asn-leu-glu-ile-thr-tyr-val-
gln-arg-asn-tyr-asp-leu-ser-phe-leu-lys-
thr-ile-gln-glu-val-ala-gly-tyr-val-leu-
ile-ala-leu-asn-thr-val-glu-arg-ile-pro-
leu-glu-asn-leu-gln-ile-ile-arg-gly-asn-
met-tyr-tyr-glu-asn-ser-tyr-ala-leu-ala-
val-leu-ser-asn-tyr-asp-ala-asn-lys-thr-
gly-leu-lys-glu-leu-pro-met-arg-asn-leu-
gln-glu-ile-leu-his-gly-ala-val-arg-phe-
ser-asn-asn-pro-ala-leu-cys-asn-val-glu-
ser-ile-gln-trp-arg-asp-ile-val-ser-ser-
asp-phe-leu-ser-asn-met-ser-met-asp-phe-
gln-asn-his-leu-gly-ser-cys-gln-lys-cys-
asp-pro-ser-cys-pro-asn-gly-ser-cys-trp-
gly-ala-gly-glu-glu-asn-cys-gln-lys-leu-
thr-lys-ile-ile-cys-ala-gln-gln-cys-ser-
gly-arg-cys-arg-gly-lys-ser-pro-ser-asp-
cys-cys-his-asn-gln-cys-ala-ala-gly-cys-
thr-gly-pro-arg-glu-ser-asp-cys-leu-val-

FIGURE 4 cys-arg-lys-phe-arg-asp-glu-ala-thr-cys-
lys-asp-thr-cys-pro-pro-leu-met-leu-tyr-
asn-pro-thr-thr-tyr-gln-met-asp-val-asn-
pro-glu-gly-lys-tyr-ser-phe-gly-ala-thr-
cys-val-lys-lys-cys-pro-arg-asn-tyr-val-
val-thr-asp-his-gly-ser-cys-val-arg-ala-
cys-gly-ala-asp-ser-tyr-glu-met-glu-glu-
asp-gly-val-arg-lys-cys-lys-lys-cys-glu-
gly-pro-cys-arg-lys-val-cys-asn-gly-ile-
gly-ile-gly-glu-phe-lys-asp-ser-leu-ser-
ile-asn-ala-thr-asn-ile-lys-his-phe-lys-
asn-cys-thr-ser-ile-ser-gly-asp-leu-his-
ile-leu-pro-val-ala-phe-arg-gly-asp-ser-
phe-thr-his-thr-pro-pro-leu-asp-pro-gln-
glu-leu-asp-ile-leu-lys-thr-val-lys-glu-
ile-thr-gly-phe-leu-leu-ile-gln-ala-trp-
pro-glu-asn-arg-thr-asp-leu-his-ala-phe-
glu-asn-leu-glu-ile-ile-arg-gly-arg-thr-
lys-gln-his-gly-gln-phe-ser-leu-ala-val-
val-ser-leu-asn-ile-thr-ser-leu-gly-leu-
arg-ser-leu-lys-glu-ile-ser-asp-gly-asp-
val-ile-ile-ser-gly-asn-lys-asn-leu-cys-
tyr-ala-asn-thr-ile-asn-trp-lys-lys-leu-
phe-gly-thr-ser-gly-gln-lys-thr-lys-ile-
ile-ser-asn-arg-gly-glu-asn-ser-cys-lys-
ala-thr-gly-gln-val-cys-his-ala-leu-cys-
ser-pro-glu-gly-cys-trp-gly-pro-glu-pro-
arg-asp-cys-val-ser-cys-arg-asn-val-STOP

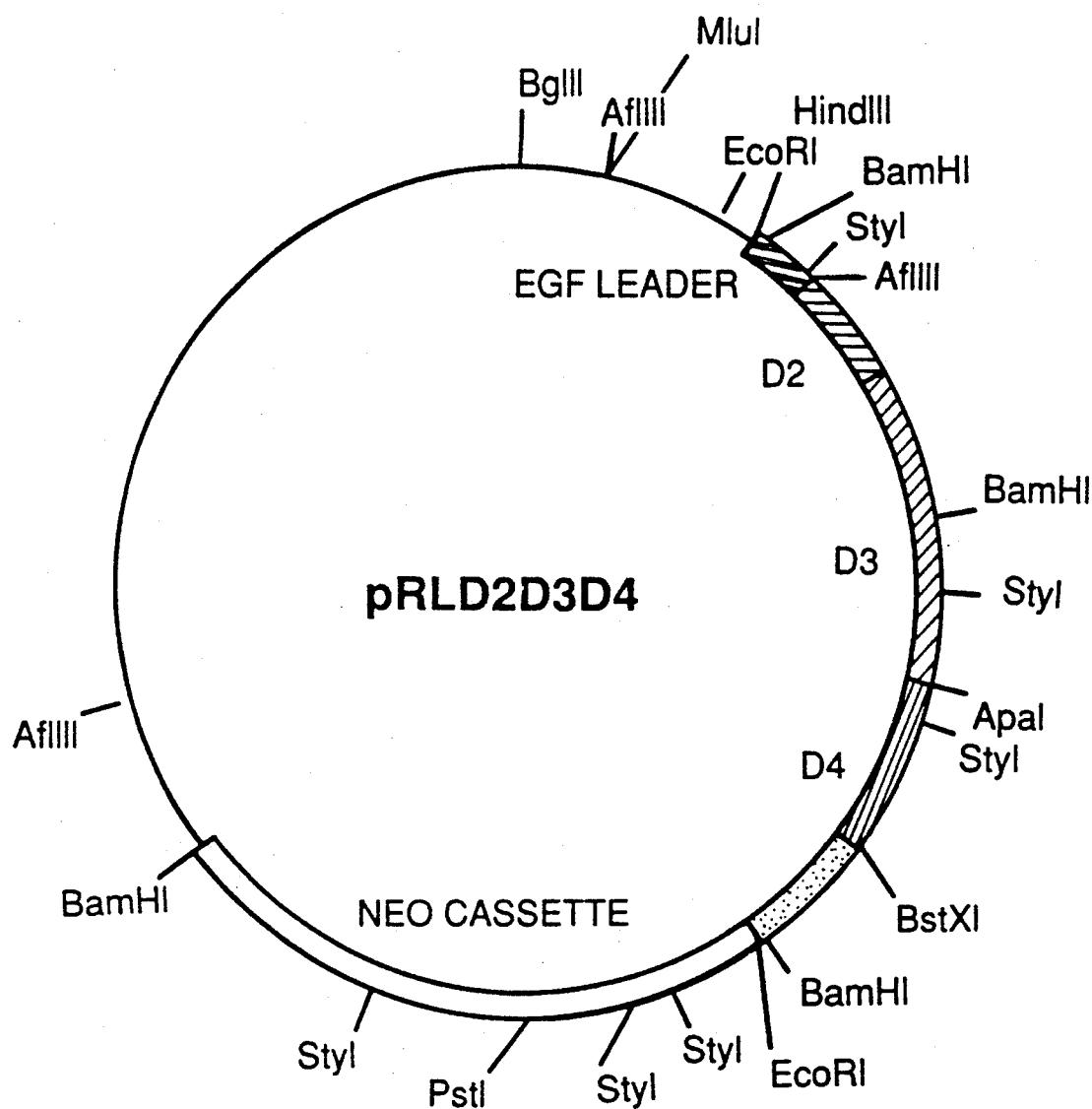
FIG. 5
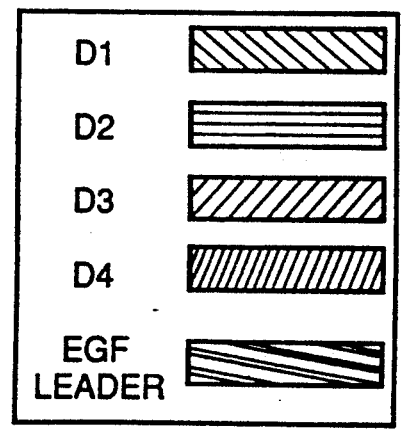

BglII
1  GACGGATCGGGAGATCTCCCGATCCCCTATGGTGCACTCTCAGTACAATC
   CTGCCTAGCCCTCTAGAGGGCTAGGGGATACCACGTGAGAGTCATGTTAG
51 TGCTCTGATGCCGCATAGTTAAGCCAGTATCTGCTCCCTGCTTGTGTGTT
   ACGAGACTACGGCGTATCAATTCGGTCATAGACGAGGGACGAACACACAA
101 GGAGGTCGCTGAGTAGTGCGCGAGCAAAATTTAAGCTACAACAAGGCAAG
    CCTCCAGCGACTCATCACGCGCTCGTTTTAAATTCGATGTTGTTCCGTTC
151 GCTTGACCGACAATTGCATGAAGAATCTGCTTAGGGTTAGGCGTTTTGCG
    CGAACTGGCTGTTAACGTACTTCTTAGACGAATCCCAATCCGCAAAACGC

MluI
afl III
201 CTGCTTCGCGATGTACGGGCCAGATATACGCGTATCTGAGGGGACTAGGG
    GACGAAGCGCTACATGCCCGGTCTATATGCGCATAGACTCCCCTGATCCC
251 TGTGTTAGGCGAAAAGCGGGGCTTCGGTTGTACGCGGTTAGGAGTCCCC
    ACACAAATCCGCTTTTCGCCCCGAAGCCAACATGCGCCAATCCTCAGGGG
301 TCAGGATATAGTAGTTTCGCTTTTGCATAGGGAGGGGGAAATGTAGTCTT
    AGTCCTATATCATCAAAGCGAAAACGTATCCCTCCCCCTTTACATCAGAA
351 ATGCAATACACTTGTAGTCTTGCAACATGGTAACGATGAGTTAGCAACAT
    TACGTTATGTGAACATCAGAACGTTGTACCATTGCTACTCAATCGTTGTA
401 GCCTTACAAGGAGAGAAAAAGCACCGTGCATGCCGATTGGTGGAAGTAAG
    CGGAATGTTCCTCTCTTTTTCGTGGCACGTACGGCTAACCACCTTCATTC
451 GTGGTACGATCGTGCCTTATTAGGAAGGCAACAGACAGGTCTGACATGGA
    CACCATGCTAGCACGGAATAATCCTTCCGTTGTCTGTCCAGACTGTACCT

EcoRI
501 TTGGACGAACCACTGAATTCCGCATTGCAGAGATAATTGTATTTAAGTGC
    AACCTGCTTGGTGACTTAAGGCGTAACGTCTCTATTAACATAAATTCACG
551 CTAGCTCGATACAATAAACGCCATTTGACCATTCACCACATTGGTGTGCA
    GATCGAGCTATGTTATTTGCGGTAAACTGGTAAGTGGTGTAACCACACGT

HindIII                    BamHI
601 CCTCCAAGCTTGGGCTGCAGGTCGACTCTAGAGGATCCCCGGGCGAGCTC
    GGAGGTTCGAACCCGACGTCCAGCTGAGATCTCCTAGGGGCCCGCTCGAG

START D2D3D4
651 TTCGGGGAGCAGCGATGCGACCCTCCGGGACGGCCGGGGCAGCGCTCCTG
    AAGCCCCTCGTCGCTACGCTGGGAGGCCCTGCCGGCCCCGTCGCGAGGAC
701 GCGCTGCGGCTGCGCTCTGCCCGGCGAGTCGGGCTCTGGAGGAAAAGAAA
    CGCGACGCCGACGCGAGACGGGCCGCTCAGCCCGAGACCTCCTTTTCTTT

StyI      afl III
751 GTTTGCCAAGGCAGCAACATGTCGATGGACTTCCAGAACCACCTGGGCAG
    CAAACGGTTCCGTCGTTGTACAGCTACCTGAAGGTCTTGGTGGACCCGTC

FIGURE 6A

```
 801 CTGCCAAAAGTGTGATCCAAGCTGTCCCAATGGGAGCTGCTGGGGTGCAG
     GACGGTTTTCACACTAGGTTCGACAGGGTTACCCTCGACGACCCCACGTC
 851 GAGAGGAGAACTGCCAGAAACTGACCAAAATCATCTGTGCCCAGCAGTGC
     CTCTCCTCTTGACGGTCTTTGACTGGTTTTAGTAGACACGGGTCGTCACG
 901 TCCGGGCGCTGCCGTGGCAAGTCCCCCAGTGACTGCTGCCACAACCAGTG
     AGGCCCGCGACGGCACCGTTCAGGGGGTCACTGACGACGGTGTTGGTCAC
 951 TGCTGCAGGCTGCACAGGCCCCCGGGAGAGCGACTGCCTGGTCTGCCGCA
     ACGACGTCCGACGTGTCCGGGGGCCCTCTCGCTGACGGACCAGACGGCGT
1001 AATTCCGAGACGAAGCCACGTGCAAGGACACCTGCCCCCCACTCATGCTC
     TTAAGGCTCTGCTTCGGTGCACGTTCCTGTGGACGGGGGGTGAGTACGAG
1051 TACAACCCCACCACGTACCAGATGGATGTGAACCCCGAGGGCAAATACAG
     ATGTTGGGGTGGTGCATGGTCTACCTACACTTGGGGCTCCCGTTTATGTC
1101 CTTTGGTGCCACCTGCGTGAAGAAGTGTCCCCGTAATTATGTGGTGACAG
     GAAACCACGGTGGACGCACTTCTTCACAGGGGCATTAATACACCACTGTC
1151 ATCACGGCTCGTGCGTCCGAGCCTGTGGGGCCGACAGCTATGAGATGGAG
     TAGTGCCGAGCACGCAGGCTCGGACACCCCGGCTGTCGATACTCTACCTC
1201 GAAGACGGCGTCCGCAAGTGTAAGAAGTGCGAAGGGCCTTGCCGCAAAGT
     CTTCTGCCGCAGGCGTTCACATTCTTCACGCTTCCCGGAACGGCGTTTCA
1251 GTGTAACGGAATAGGTATTGGTGAATTTAAAGACTCACTCTCCATAAATG
     CACATTGCCTTATCCATAACCACTTAAATTTCTGAGTGAGAGGTATTTAC
1301 CTACGAATATTAAACACTTCAAAAACTGCACCTCCATCAGTGGCGATCTC
     GATGCTTATAATTTGTGAAGTTTTTGACGTGGAGGTAGTCACCGCTAGAG
1351 CACATCCTGCCGGTGGCATTTAGGGGTGACTCCTTCACACATACTCCTCC
     GTGTAGGACGGCCACCGTAAATCCCCACTGAGGAAGTGTGTATGAGGAGG
     BamHI
1401 TCTGGATCCACAGGAACTGGATATTCTGAAAACCGTAAAGGAAATCACAG
     AGACCTAGGTGTCCTTGACCTATAAGACTTTTGGCATTTCCTTTAGTGTC
1451 GGTTTTTGCTGATTCAGGCTTGGCCTGAAAACAGGACGGACCTCCATGCC
     CCAAAAACGACTAAGTCCGAACCGGACTTTTGTCCTGCCTGGAGGTACGG
1501 TTTGAGAACCTAGAAATCARACGCGGCAGGACCAAGCAACATGGTCAGTT
     AAACTCTTGGATCTTTAGTYTGCGCCGTCCTGGTTCGTTGTACCAGTCAA
                                            StyI
1551 TTCTCTTGCAGTCGTCAGCCTGAACATAACATCCTTGGGATTACGCTCCC
     AAGAGAACGTCAGCAGTCGGACTTGTATTGTAGGACCCTAATGCGAGGG
1601 TCAAGGAGATAAGTGATGGAGATGTGATAATTTCAGGAAACAAAAATTTG
     AGTTCCTCTATTCACTACCTCTACACTATTAAAGTCCTTTGTTTTTAAAC
                                       PpuMI
1651 TGCTATGCAAATACAATAAACTGGAAAAAACTGTTTGGGACCTCCGGTCA
     ACGATACGTTTATGTTATTTGACCTTTTTTGACAAACCCTGGAGGCCAGT
```

FIGURE 6B

```
1701 GAAAACCAAAATTATAAGCAACAGAGGTGAAAACAGCTGCAAGGCCACAG
     CTTTTGGTTTTAATATTCGTTGTCTCCACTTTTGTCGACGTTCCGGTGTC
                                                                    ApaI
1751 GCCAGGTCTGCCATGCCTTGTGCTCCCCCGAGGGCTGCTGGGGCCCGGAG
     CGGTCCAGACGGTACGGAACACGAGGGGGCTCCCGACGACCCCGGGCCTC
1801 CCCAGGGACTGCGTCTCTTGCCGGAATGTCAGCCGAGGCAGGGAATGCGT
     GGGTCCCTGACGCAGAGAACGGCCTTACAGTCGGCTCCGTCCCTTACGCA
                            StyI
1851 GGACAAGTGCAACCTTCTGGAGGGTGAGCCAAGGGAGTTTGTGGAGAACT
     CCTGTTCACGTTGGAAGACCTCCCACTCGGTTCCCTCAAACACCTCTTGA
1901 CTGAGTGCATACAGTGCCACCCAGAGTGCCTGCCTCAGGCCATGAACATC
     GACTCACGTATGTCACGGTGGGTCTCACGGACGGAGTCCGGTACTTGTAG
1951 ACCTGCACAGGACGGGGACCAGACAACTGTATCCAGTGTGCCCACTACAT
     TGGACGTGTCCTGCCCCTGGTCTGTTGACATAGGTCACACGGGTGATGTA
2001 TGACGGCCCCCACTGCGTCAAGACCTGCCCGGCAGGAGTCATGGGAGAAA
     ACTGCCGGGGGTGACGCAGTTCTGGACGGGCCGTCCTCAGTACCCTCTTT
2051 ACAACACCCTGGTCTGGAAGTACGCAGACGCCGGCCATGTGTGCCACCTG
     TGTTGTGGGACCAGACCTTCATGCGTCTGCGGCCGGTACACACGGTGGAC
2101 TGCCATCCAAACTGCACCTACGGATGCACTGGGCCAGGTCTTGAAGGCTG
     ACGGTAGGTTTGACGTGGATGCCTACGTGACCCGGTCCAGAACTTCCGAC
                                                      BstXI
                                                STOP D2D3D4
2151 TCCAACGAATGGGCCTAAGATCCCGTCCATCGCCACTGGGTGACCAGCAC
     AGGTTGCTTACCCGGATTCTAGGGCAGGTAGCGGTGACCCACTGGTCGTG
2201 AATGGATCTCGAGGTCGAGGGATCTCTAGAGCTCGCTGATCAGCCTCGAC
     TTACCTAGAGCTCCAGCTCCCTAGAGATCTCGAGCGACTAGTCGGAGCTG
2251 TGTGCCTTCTAGTTGCCAGCCATCTGTTGTTTGCCCCTCCCCCGTGCCTT
     ACACGGAAGATCAACGGTCGGTAGACAACAAACGGGGAGGGGGCACGGAA
2301 CCTTGACCCTGGAAGGTGCCACTCCCACTGTCCTTTCCTAATAAAATGAG
     GGAACTGGGACCTTCCACGGTGAGGGTGACAGGAAAGGATTATTTTACTC
2351 GAAATTGCATCGCATTGTCTGAGTAGGTGTCATTCTATTCTGGGGGGTGG
     CTTTAACGTAGCGTAACAGACTCATCCACAGTAAGATAAGACCCCCCACC
2401 GGTGGGGCAGGACAGCAAGGGGGAGGATTGGGAAGACAATAGCAGGCATG
     CCACCCCGTCCTGTCGTTCCCCCTCCTAACCCTTCTGTTATCGTCCGTAC
                                            BamHI
2451 CTGGGGATGCGGTGGGCTCTATGGAACCAGCTGGGGCTCGAGGGGGGATC
     GACCCCTACGCCACCCGAGATACCTTGGTCGACCCCGAGCTCCCCCCTAG
     EcoRI
2501 CCCGGGAATTCTGTGGAATGTGTGTCAGTTAGGGTGTGGAAAGTCCCCAG
     GGGCCCTTAAGACACCTTACACACAGTCAATCCCACACCTTTCAGGGGTC
```

FIGURE 6C

```
2551 GCTCCCCAGCAGGCAGAAGTATGCAAAGCATGCATCTCAATTAGTCAGCA
     CGAGGGGTCGTCCGTCTTCATACGTTTCGTACGTAGAGTTAATCAGTCGT
2601 ACCAGGTGTGGAAAGTCCCCAGGCTCCCCAGCAGGCAGAAGTATGCAAAG
     TGGTCCACACCTTTCAGGGGTCCGAGGGGTCGTCCGTCTTCATACGTTTC
2651 CATGCATCTCAATTAGTCAGCAACCATAGTCCCGCCCCTAACTCCGCCCA
     GTACGTAGAGTTAATCAGTCGTTGGTATCAGGGCGGGGATTGAGGCGGGT
                                                  StyI
2701 TCCCGCCCCTAACTCCGCCCAGTTCCGCCCATTCTCCGCCCCATGGCTGA
     AGGGCGGGGATTGAGGCGGGTCAAGGCGGGTAAGAGGCGGGGTACCGACT
2751 CTAATTTTTTTATTTATGCAGAGGCCGAGGCCGCCTCGGCCTCTGAGCT
     GATTAAAAAAAATAAATACGTCTCCGGCTCCGGCGGAGCCGGAGACTCGA
                                              StyI
2801 ATTCCAGAAGTAGTGAGGAGGCTTTTTGGAGGCCTAGGCTTTTGCAAAA
     TAAGGTCTTCATCACTCCTCCGAAAAAACCTCCGGATCCGAAAACGTTTT
2851 AGCTCCCGGGAGCTTGGATATCCATTTTCGGATCTGATCAAGAGACAGGA
     TCGAGGGCCCTCGAACCTATAGGTAAAAGCCTAGACTAGTTCTCTGTCCT
2901 TGAGGATCGTTTCGCATGATTGAACAAGATGGATTGCACGCAGGTTCTCC
     ACTCCTAGCAAAGCGTACTAACTTGTTCTACCTAACGTGCGTCCAAGAGG
2951 GGCCGCTTGGGTGGAGAGGCTATTCGGCTATGACTGGGCACAACAGACAA
     CCGGCGAACCCACCTCTCCGATAAGCCGATACTGACCCGTGTTGTCTGTT
                                              NarI
3001 TCGGCTGCTCTGATGCCGCCGTGTTCCGGCTGTCAGCGCAGGGGCGCCCG
     AGCCGACGAGACTACGGCGGCACAAGGCCGACAGTCGCGTCCCCGCGGGC
                                              PstI
3051 GTTCTTTTTGTCAAGACCGACCTGTCCGGTGCCCTGAATGAACTGCAGGA
     CAAGAAAAACAGTTCTGGCTGGACAGGCCACGGGACTTACTTGACGTCCT
3101 CGAGGCAGCGCGGCTATCGTGGCTGGCCACGACGGGCGTTCCTTGCGCAG
     GCTCCGTCGCGCCGATAGCACCGACCGGTGCTGCCCGCAAGGAACGCGTC
3151 CTGTGCTCGACGTTGTCACTGAAGCGGGAAGGGACTGGCTGCTATTGGGC
     GACACGAGCTGCAACAGTGACTTCGCCCTTCCCTGACCGACGATAACCCG
3201 GAAGTGCCGGGGCAGGATCTCCTGTCATCTCACCTTGCTCCTGCCGAGAA
     CTTCACGGCCCCGTCCTAGAGGACAGTAGAGTGGAACGAGGACGGCTCTT
3251 AGTATCCATCATGGCTGATGCAATGCGGCGGCTGCATACGCTTGATCCGG
     TCATAGGTAGTACCGACTACGTTACGCCGCCGACGTATGCGAACTAGGCC
3301 CTACCTGCCCATTCGACCACCAAGCGAAACATCGCATCGAGCGAGCACGT
     GATGGACGGGTAAGCTGGTGGTTCGCTTTGTAGCGTAGCTCGCTCGTGCA
3351 ACTCGGATGGAAGCCGGTCTTGTCGATCAGGATGATCTGGACGAAGAGCA
     TGAGCCTACCTTCGGCCAGAACAGCTAGTCCTACTAGACCTGCTTCTCGT
3401 TCAGGGGCTCGCGCCAGCCGAACTGTTCGCCAGGCTCAAGGCGCGCATGC
     AGTCCCCGAGCGCGGTCGGCTTGACAAGCGGTCCGAGTTCCGCGCGTACG
```

FIGURE 6D

```
                                         StyI
3451 CCGACGGCGAGGATCTCGTCGTGACCCATGGCGATGCCTGCTTGCCGAAT
     GGCTGCCGCTCCTAGAGCAGCACTGGGTACCGCTACGGACGAACGGCTTA
3501 ATCATGGTGGAAAATGGCCGCTTTTCTGGATTCATCGACTGTGGCCGGCT
     TAGTACCACCTTTTACCGGCGAAAAGACCTAAGTAGCTGACACCGGCCGA
3551 GGGTGTGGCGGACCGCTATCAGGACATAGCGTTGGCTACCCGTGATATTG
     CCCACACCGCCTGGCGATAGTCCTGTATCGCAACCGATGGGCACTATAAC
3601 CTGAAGAGCTTGGCGGCGAATGGGCTGACCGCTTCCTCGTGCTTTACGGT
     GACTTCTCGAACCGCCGCTTACCCGACTGGCGAAGGAGCACGAAATGCCA
3651 ATCGCCGCTCCCGATTCGCAGCGCATCGCCTTCTATCGCCTTCTTGACGA
     TAGCGGCGAGGGCTAAGCGTCGCGTAGCGGAAGATAGCGGAAGAACTGCT
3701 GTTCTTCTGAGCGGGACTCTGGGGTTCGAAATGACCGACCAAGCGACGCC
     CAAGAAGACTCGCCCTGAGACCCCAAGCTTTACTGGCTGGTTCGCTGCGG
3751 CAACCTGCCATCACGAGATTTCGATTCCACCGCCGCCTTCTATGAAAGGT
     GTTGGACGGTAGTGCTCTAAAGCTAAGGTGGCGGCGGAAGATACTTTCCA
3801 TGGGCTTCGGAATCGTTTTCCGGGACGCCGGCTGGATGATCCTCCAGCGC
     ACCCGAAGCCTTAGCAAAAGGCCCTGCGGCCGACCTACTAGGAGGTCGCG
3851 GGGGATCTCATGCTGGAGTTCTTCGCCCACCCCAACTTGTTTATTGCAGC
     CCCCTAGAGTACGACCTCAAGAAGCGGGTGGGGTTGAACAAATAACGTCG
3901 TTATAATGGTTACAAATAAAGCAATAGCATCACAAATTTCACAAATAAAG
     AATATTACCAATGTTTATTTCGTTATCGTAGTGTTTAAAGTGTTTATTTC
3951 CATTTTTTTCACTGCATTCTAGTTGTGGTTTGTCCAAACTCATCAATGTA
     GTAAAAAAAGTGACGTAAGATCAACACCAAACAGGTTTGAGTAGTTACAT
                          BamHI
4001 TCTTATCATGTCTGGATCCCGTCGACCTCGAGAGCTTGGCGTAATCATGG
     AGAATAGTACAGACCTAGGGCAGCTGGAGCTCTCGAACCGCATTAGTACC
4051 TCATAGCTGTTTCCTGTGTGAAATTGTTATCCGCTCACAATTCCACACAA
     AGTATCGACAAAGGACACACTTTAACAATAGGCGAGTGTTAAGGTGTGTT
4101 CATACGAGCCGGAAGCATAAAGTGTAAAGCCTGGGGTGCCTAATGAGTGA
     GTATGCTCGGCCTTCGTATTTCACATTTCGGACCCCACGGATTACTCACT
4151 GCTAACTCACATTAATTGCGTTGCGCTCACTGCCCGCTTTCCAGTCGGGA
     CGATTGAGTGTAATTAACGCAACGCGAGTGACGGGCGAAAGGTCAGCCCT
4201 AACCTGTCGTGCCAGCTGCATTAATGAATCGGCCAACGCGCGGGGAGAGG
     TTGGACAGCACGGTCGACGTAATTACTTAGCCGGTTGCGCGCCCCTCTCC
4251 CGGTTTGCGTATTGGGCGCTCTTCCGCTTCCTCGCTCACTGACTCGCTGC
     GCCAAACGCATAACCCGCGAGAAGGCGAAGGAGCGAGTGACTGAGCGACG
4301 GCTCGGTCGTTCGGCTGCGGCGAGCGGTATCAGCTCACTCAAAGGCGGTA
     CGAGCCAGCAAGCCGACGCCGCTCGCCATAGTCGAGTGAGTTTCCGCCAT
```

FIGURE 6E afl III
4351 ATACGGTTATCCACAGAATCAGGGGATAACGCAGGAAAGAACATGTGAGC
     TATGCCAATAGGTGTCTTAGTCCCCTATTGCGTCCTTTCTTGTACACTCG
4401 AAAAGGCCAGCAAAAGGCCAGGAACCGTAAAAAGGCCGCGTTGCTGGCGT
     TTTTCCGGTCGTTTTCCGGTCCTTGGCATTTTTCCGGCGCAACGACCGCA
4451 TTTTCCATAGGCTCCGCCCCCCTGACGAGCATCACAAAAATCGACGCTCA
     AAAAGGTATCCGAGGCGGGGGGACTGCTCGTAGTGTTTTTAGCTGCGAGT
4501 AGTCAGAGGTGGCGAAACCCGACAGGACTATAAAGATACCAGGCGTTTCC
     TCAGTCTCCACCGCTTTGGGCTGTCCTGATATTTCTATGGTCCGCAAAGG
4551 CCCTGGAAGCTCCCTCGTGCGCTCTCCTGTTCCGACCCTGCCGCTTACCG
     GGGACCTTCGAGGGAGCACGCGAGAGGACAAGGCTGGGACGGCGAATGGC
4601 GATACCTGTCCGCCTTTCTCCCTTCGGGAAGCGTGGCGCTTTCTCAATGC
     CTATGGACAGGCGGAAAGAGGGAAGCCCTTCGCACCGCGAAAGAGTTACG
4651 TCACGCTGTAGGTATCTCAGTTCGGTGTAGGTCGTTCGCTCCAAGCTGGG
     AGTGCGACATCCATAGAGTCAAGCCACATCCAGCAAGCGAGGTTCGACCC
4701 CTGTGTGCACGAACCCCCCGTTCAGCCCGACCGCTGCGCCTTATCCGGTA
     GACACACGTGCTTGGGGGGCAAGTCGGGCTGGCGACGCGGAATAGGCCAT
4751 ACTATCGTCTTGAGTCCAACCCGGTAAGACACGACTTATCGCCACTGGCA
     TGATAGCAGAACTCAGGTTGGGCCATTCTGTGCTGAATAGCGGTGACCGT
4801 GCAGCCACTGGTAACAGGATTAGCAGAGCGAGGTATGTAGGCGGTGCTAC
     CGTCGGTGACCATTGTCCTAATCGTCTCGCTCCATACATCCGCCACGATG
4851 AGAGTTCTTGAAGTGGTGGCCTAACTACGGCTACACTAGAAGGACAGTAT
     TCTCAAGAACTTCACCACCGGATTGATGCCGATGTGATCTTCCTGTCATA
4901 TTGGTATCTGCGCTCTGCTGAAGCCAGTTACCTTCGGAAAAAGAGTTGGT
     AACCATAGACGCGAGACGACTTCGGTCAATGGAAGCCTTTTTCTCAACCA
4951 AGCTCTTGATCCGGCAAACAAACCACCGCTGGTAGCGGTGGTTTTTTTGT
     TCGAGAACTAGGCCGTTTGTTTGGTGGCGACCATCGCCACCAAAAAAACA
5001 TTGCAAGCAGCAGATTACGCGCAGAAAAAAAGGATCTCAAGAAGATCCTT
     AACGTTCGTCGTCTAATGCGCGTCTTTTTTTCCTAGAGTTCTTCTAGGAA
5051 TGATCTTTTCTACGGGGTCTGACGCTCAGTGGAACGAAAACTCACGTTAA
     ACTAGAAAAGATGCCCCAGACTGCGAGTCACCTTGCTTTTGAGTGCAATT
5101 GGGATTTTGGTCATGAGATTATCAAAAAGGATCTTCACCTAGATCCTTTT
     CCCTAAAACCAGTACTCTAATAGTTTTTCCTAGAAGTGGATCTAGGAAAA
5151 AAATTAAAAATGAAGTTTTAAATCAATCTAAAGTATATATGAGTAAACTT
     TTTAATTTTTACTTCAAAATTTAGTTAGATTTCATATATACTCATTTGAA
5201 GGTCTGACAGTTACCAATGCTTAATCAGTGAGGCACCTATCTCAGCGATC
     CCAGACTGTCAATGGTTACGAATTAGTCACTCCGTGGATAGAGTCGCTAG
5251 TGTCTATTTCGTTCATCCATAGTTGCCTGACTCCCCGTCGTGTAGATAAC
     ACAGATAAAGCAAGTAGGTATCAACGGACTGAGGGGCAGCACATCTATTG

FIGURE 6F

```
5301 TACGATACGGGAGGGCTTACCATCTGGCCCCAGTGCTGCAATGATACCGC
     ATGCTATGCCCTCCCGAATGGTAGACCGGGGTCACGACGTTACTATGGCG
5351 GAGACCCACGCTCACCGGCTCCAGATTTATCAGCAATAAACCAGCCAGCC
     CTCTGGGTGCGAGTGGCCGAGGTCTAAATAGTCGTTATTTGGTCGGTCGG
5401 GGAAGGGCCGAGCGCAGAAGTGGTCCTGCAACTTTATCCGCCTCCATCCA
     CCTTCCCGGCTCGCGTCTTCACCAGGACGTTGAAATAGGCGGAGGTAGGT
5451 GTCTATTAATTGTTGCCGGGAAGCTAGAGTAAGTAGTTCGCCAGTTAATA
     CAGATAATTAACAACGGCCCTTCGATCTCATTCATCAAGCGGTCAATTAT
5501 GTTTGCGCAACGTTGTTGCCATTGCTACAGGCATCGTGGTGTCACGCTCG
     CAAACGCGTTGCAACAACGGTAACGATGTCCGTAGCACCACAGTGCGAGC
5551 TCGTTTGGTATGGCTTCATTCAGCTCCGGTTCCCAACGATCAAGGCGAGT
     AGCAAACCATACCGAAGTAAGTCGAGGCCAAGGGTTGCTAGTTCCGCTCA
5601 TACATGATCCCCCATGTTGTGCAAAAAAGCGGTTAGCTCCTTCGGTCCTC
     ATGTACTAGGGGGTACAACACGTTTTTTCGCCAATCGAGGAAGCCAGGAG
5651 CGATCGTTGTCAGAAGTAAGTTGGCCGCAGTGTTATCACTCATGGTTATG
     GCTAGCAACAGTCTTCATTCAACCGGCGTCACAATAGTGAGTACCAATAC
5701 GCAGCACTGCATAATTCTCTTACTGTCATGCCATCCGTAAGATGCTTTTC
     CGTCGTGACGTATTAAGAGAATGACAGTACGGTAGGCATTCTACGAAAAG
5751 TGTGACTGGTGAGTACTCAACCAAGTCATTCTGAGAATAGTGTATGCGGC
     ACACTGACCACTCATGAGTTGGTTCAGTAAGACTCTTATCACATACGCCG
5801 GACCGAGTTGCTCTTGCCCGGCGTCAATACGGGATAATACCGCGCCACAT
     CTGGCTCAACGAGAACGGGCCGCAGTTATGCCCTATTATGGCGCGGTGTA
5851 AGCAGAACTTTAAAAGTGCTCATCATTGGAAAACGTTCTTCGGGGCGAAA
     TCGTCTTGAAATTTTCACGAGTAGTAACCTTTTGCAAGAAGCCCCGCTTT
5901 ACTCTCAAGGATCTTACCGCTGTTGAGATCCAGTTCGATGTAACCCACTC
     TGAGAGTTCCTAGAATGGCGACAACTCTAGGTCAAGCTACATTGGGTGAG
5951 GTGCACCCAACTGATCTTCAGCATCTTTTACTTTCACCAGCGTTTCTGGG
     CACGTGGGTTGACTAGAAGTCGTAGAAAATGAAAGTGGTCGCAAAGACCC
6001 TGAGCAAAAACAGGAAGGCAAAATGCCGCAAAAAGGGAATAAGGGCGAC
     ACTCGTTTTTGTCCTTCCGTTTTACGGCGTTTTTCCCTTATTCCCGCTG
6051 ACGGAAATGTTGAATACTCATACTCTTCCTTTTTCAATATTATTGAAGCA
     TGCCTTTACAACTTATGAGTATGAGAAGGAAAAAGTTATAATAACTTCGT
6101 TTTATCAGGGTTATTGTCTCATGAGCGGATACATATTTGAATGTATTTAG
     AAATAGTCCCAATAACAGAGTACTCGCCTATGTATAAACTTACATAAATC
6151 AAAAATAAACAAATAGGGGTTCCGCGCACATTTCCCCGAAAAGTGCCACC
     TTTTTATTTGTTTATCCCCAAGGCGCGTGTAAAGGGGCTTTTCACGGTGG
6201 TGACGTC
     ACTGCAG
```

FIGURE 6G

OPEN READING FRAME ANALYSIS

DNA> pRLD2D3D4/DI2 starts at nt #: +665
number of amino acids: 509
molecular weight: 54955

Three letter representation:
-24
met-arg-pro-ser-gly-thr-ala-gly-ala-ala-
leu-leu-ala-leu-leu-ala-ala-leu-cys-pro-

+1 ala-ser-arg-ala-leu-glu-glu-lys-lys-val-

+9  +150 cys-gln-gly-ser-asn-met-ser-met-asp-phe-
gln-asn-his-leu-gly-ser-cys-gln-lys-cys-
asp-pro-ser-cys-pro-asn-gly-ser-cys-trp-
gly-ala-gly-glu-glu-asn-cys-gln-lys-leu-
thr-lys-ile-ile-cys-ala-gln-gln-cys-ser-
gly-arg-cys-arg-gly-lys-ser-pro-ser-asp-
cys-cys-his-asn-gln-cys-ala-ala-gly-cys-
thr-gly-pro-arg-glu-ser-asp-cys-leu-val-
cys-arg-lys-phe-arg-asp-glu-ala-thr-cys-
lys-asp-thr-cys-pro-pro-leu-met-leu-tyr-
asn-pro-thr-thr-tyr-gln-met-asp-val-asn-
pro-glu-gly-lys-tyr-ser-phe-gly-ala-thr-
cys-val-lys-lys-cys-pro-arg-asn-tyr-val-
val-thr-asp-his-gly-ser-cys-val-arg-ala-
cys-gly-ala-asp-ser-tyr-glu-met-glu-glu-
asp-gly-val-arg-lys-cys-lys-lys-cys-glu-
gly-pro-cys-arg-lys-val-cys-asn-gly-ile-
gly-ile-gly-glu-phe-lys-asp-ser-leu-ser-
ile-asn-ala-thr-asn-ile-lys-his-phe-lys-
asn-cys-thr-ser-ile-ser-gly-asp-leu-his-

FIGURE 7 ile-leu-pro-val-ala-phe-arg-gly-asp-ser-
phe-thr-his-thr-pro-pro-leu-asp-pro-gln-
glu-leu-asp-ile-leu-lys-thr-val-lys-glu-
ile-thr-gly-phe-leu-leu-ile-gln-ala-trp-
pro-glu-asn-arg-thr-asp-leu-his-ala-phe-
glu-asn-leu-glu-ile-ile-arg-gly-arg-thr-
lys-gln-his-gly-gln-phe-ser-leu-ala-val-
val-ser-leu-asn-ile-thr-ser-leu-gly-leu-
arg-ser-leu-lys-glu-ile-ser-asp-gly-asp-
val-ile-ile-ser-gly-asn-lys-asn-leu-cys-
tyr-ala-asn-thr-ile-asn-trp-lys-lys-leu-
phe-gly-thr-ser-gly-gln-lys-thr-lys-ile-
ile-ser-asn-arg-gly-glu-asn-ser-cys-lys-
ala-thr-gly-gln-val-cys-his-ala-leu-cys-
ser-pro-glu-gly-cys-trp-gly-pro-glu-pro-
arg-asp-cys-val-ser-cys-arg-asn-val-ser-
arg-gly-arg-glu-cys-val-asp-lys-cys-asn-
leu-leu-glu-gly-glu-pro-arg-glu-phe-val-
glu-asn-ser-glu-cys-ile-gln-cys-his-pro-
glu-cys-leu-pro-gln-ala-met-asn-ile-thr-
cys-thr-gly-arg-gly-pro-asp-asn-cys-ile-
gln-cys-ala-his-tyr-ile-asp-gly-pro-his-
cys-val-lys-thr-cys-pro-ala-gly-val-met-
gly-glu-asn-asn-thr-leu-val-trp-lys-tyr-
ala-asp-ala-gly-his-val-cys-his-leu-cys-
his-pro-asn-cys-thr-tyr-gly-cys-thr-gly-
pro-gly-leu-glu-gly-cys-pro-thr-asn-gly-
pro-lys-ile-pro-ser-ile-ala-thr-gly-STOP

```
  1  GA CGGA TCGGGAGA TCT CCCGA TCCCC TA TGGTGCA CT CT CAGT
     CT GCC TAG CCC T C TAGA GGG C TAG GGGA TA CCA CGT GAGA GT CA
 45  A CA A TC TGC T C TGA TGCC GCA TAG TTAAG CCAG TA TC TGC T CCC
     TGT TAGA CGAGA C TA CGG CGTA T CA A TT CGG T CA TAGA C GAG GG
 89  TGC T T GT GT GT T GGA GGT CGC T GAG TAG T GCGC GAG CAAA A TTT
     A CGA A CA CA CA A CC T CCAG CGA C T CA T CA CGCGC T CGT T T T AAA
133  AAG C TA CA A CAAG GCA AGG C T T GA CC GA CA A TT GCA T GAAGAA T
     T T CGA TGT T GT T CCGT T CCGA A C TGG C TGT T AA CGTA C T T C T TA
177  C T GC T TAG GGT TAGG CGT T T T GC GC TGC T T CGC GA TGTA CGGGC
     GA CGA A T CCCA A T CC GCA AAA CGC GA C GAAG CGC TA CA TGCCCG
                                          AflIII
                                          MluI
221  CAGA TA TA CGC GTA TC T GAG GGGA C TAG GGT GT GT T T AGG CGAA
     GT C TA TA T GCG CA TAGA C T CCCC T GA T CCCA CA CA AA T CCGC T T
265  AAG CGG GGC T T CGG T T GTA CGC GGT TAG GAG T CCCC T CAGGA TA
     T T CGC CCC GAAG CCA A CA T GCG CCA A T CC T CAGGGG AG T CC TA T
309  TAG TAG T T T CGC T T T T GCA TAG GGA GGG GGA AA T GTA GT C T TA T
     A T CA T CAAAG CGA AAA CGTA T CCC T CCCCC T T TA CA T CAGAA TA
353  GCA A TA CA C T T GTA GT C T T GCA A CA T GGTA A CGA T GAG T TAG CA
     CGT TA T GT GA A CA T CAGA A CGT T GTA CCA T TGC TA C T CAA T CGT
397  A CA T GCC T TA CAAG GAGA GAAAAAG CA CCGT GCA T GCC GA T T GG
     T GTA CGGA A TGT T CC T C T C T T T T T CGT GGCA CGTA C GGC TAA CC
441  T GGAAG TAAG GT GGTA CGA T CGT GCC T TA T TAGG AAGG CAA CAG
     A CC T T CA T T CCA CCA T GC TAG CA CGGA A TAA T CC T T CCGT T GT C
                                         EcoRI
485  A CAGGT C TGA CA T GGA T TGGA CGA A CCA C T GAA T T CCGCA T T GC
     T GT CCAGA C TGTA CC TA A CC T GC T T GGT GA C T T AAGG CGTA A CG
529  AGAGA TAA T T GTA T T TAAG T GCC TAG C T CGA TA CA A TAAA CGCC
     T C T C TA T TAA CA TAAA T T CA CGGA T CGAG C TA T GT TA T T T GCGG
                                         HindIII
573  A T T T GA CCA T T CA CCA CA T T GGT GT GCA CC T CCAAG C T T GGG C T
     TAAA C T GGTAAG T GGT GTA A CCA CA CGT GGAG GT T CGA A CCC GA
                     BamHI
617  GCAGGT CGA C T C TAGA GGA T CCCC GGG CGAG C T C T T CGGGGAG C
     CGT CCAG C T GAGA T C T CC TAGG GGC CCG C T CGAGAAG CCCC T CG
```

FIGURE 9 A

START D3D4
```
 661 AGCGATGCGACCCTCCGGGACGGCCGGGGCAGCGCTCCTGGCGC
     TCGCTACGCTGGGAGGCCCTGCCGGCCCCGTCGCGAGGACCGCG
 705 TGCTGGCTGCGCTCTGCCCGGCGAGTCGGGCTCTGGAGGAAAAG
     ACGACCGACGCGAGACGGGCCGCTCAGCCCGAGACCTCCTTTTC
 749 AAAGTTTGCCAAGGTGGCGTCCGCAAGTGTAAGAAGTGCGAAGG
     TTTCAAACGGTTCCACCGCAGGCGTTCACATTCTTCACGCTTCC
 793 GCCTTGCCGCAAAGTGTGTAACGGAATAGGTATTGGTGAATTTA
     CGGAACGGCGTTTCACACATTGCCTTATCCATAACCACTTAAAT
 837 AAGACTCACTCTCCATAAATGCTACGAATATTAAACACTTCAAA
     TTCTGAGTGAGAGGTATTTACGATGCTTATAATTTGTGAAGTTT
 881 AACTGCACCTCCATCAGTGGCGATCTCCACATCCTGCCGGTGGC
     TTGACGTGGAGGTAGTCACCGCTAGAGGTGTAGGACGGCCACCG
                                                   BamHI
 925 ATTTAGGGGTGACTCCTTCACACATACTCCTCCTCTGGATCCAC
     TAAATCCCCACTGAGGAAGTGTGTATGAGGAGGAGACCTAGGTG
 969 AGGAACTGGATATTCTGAAAACCGTAAAGGAAATCACAGGGTTT
     TCCTTGACCTATAAGACTTTTGGCATTTCCTTTAGTGTCCCAAA
1013 TTGCTGATTCAGGCTTGGCCTGAAAACAGGACGGACCTCCATGC
     AACGACTAAGTCCGAACCGGACTTTTGTCCTGCCTGGAGGTACG
1057 CTTTGAGAACCTAGAAATCARACGCGGCAGGACCAAGCAACATG
     GAAACTCTTGGATCTTTAGTYTGCGCCGTCCTGGTTCGTTGTAC
                                                    StyI
1101 GTCAGTTTTCTCTTGCAGTCGTCAGCCTGAACATAACATCCTTG
     CAGTCAAAAGAGAACGTCAGCAGTCGGACTTGTATTGTAGGAAC
1145 GGATTACGCTCCCTCAAGGAGATAAGTGATGGAGATGTGATAAT
     CCTAATGCGAGGGAGTTCCTCTATTCACTACCTCTACACTATTA
1189 TTCAGGAAACAAAAATTTGTGCTATGCAAATACAATAAACTGGA
     AAGTCCTTTGTTTTTAAACACGATACGTTTATGTTATTTGACCT
1233 AAAAACTGTTTGGGACCTCCGGTCAGAAAACCAAAATTATAAGC
     TTTTTGACAAACCCTGGAGGCCAGTCTTTTGGTTTTAATATTCG
1277 AACAGAGGTGAAAACAGCTGCAAGGCCACAGGCCAGGTCTGCCA
     TTGTCTCCACTTTTGTCGACGTTCCGGTGTCCGGTCCAGACGGT
```

FIGURE 9B

```
                                            Apal            StyI
1321 TGCCTTGTGCTCCCCCGAGGGCTGCTGGGGCCCGGAGCCCAAGG
     ACGGAACACGAGGGGGCTCCCGACGACCCCGGGCCTCGGGTTCC
1365 ACTGCGTCTCTTGCCGGAATGTCAGCCGAGGCAGGGAATGCGTG
     TGACGCAGAGAACGGCCTTACAGTCGGCTCCGTCCCTTACGCAC
                              StyI
1409 GACAAGTGCAACCTTCTGGAGGGTGAGCCAAGGGAGTTTGTGGA
     CTGTTCACGTTGGAAGACCTCCCACTCGGTTCCCTCAAACACCT
1453 GAACTCTGAGTGCATACAGTGCCACCCAGAGTGCCTGCCTCAGG
     CTTGAGACTCACGTATGTCACGGTGGGTCTCACGGACGGAGTCC
1497 CCATGAACATCACCTGCACAGGACGGGGACCAGACAACTGTATC
     GGTACTTGTAGTGGACGTGTCCTGCCCCTGGTCTGTTGACATAG
1541 CAGTGTGCCCACTACATTGACGGCCCCCACTGCGTCAAGACCTG
     GTCACACGGGTGATGTAACTGCCGGGGGTGACGCAGTTCTGGAC
1585 CCCGGCAGGAGTCATGGGAGAAAACAACACCCTGGTCTGGAAGT
     GGGCCGTCCTCAGTACCCTCTTTTGTTGTGGGACCAGACCTTCA
1629 ACGCAGACGCCGGCCATGTGTGCCACCTGTGCCATCCAAACTGC
     TGCGTCTGCGGCCGGTACACACGGTGGACACGGTAGGTTTGACG
1673 ACCTACGGATGCACTGGGCCAGGTCTTGAAGGCTGTCCAACGAA
     TGGATGCCTACGTGACCCGGTCCAGAACTTCCGACAGGTTGCTT
                                       STOP D3D4
                                       BstXI
1717 TGGGCCTAAGATCCCGTCCATCGCCACTGGGTGACCAGCACAAT
     ACCCGGATTCTAGGGCAGGTAGCGGTGACCCACTGGTCGTGTTA
1761 GGATCTCGAGGTCGAGGGATCTCTAGAGCTCGCTGATCAGCCTC
     CCTAGAGCTCCAGCTCCCTAGAGATCTCGAGCGACTAGTCGGAG
1805 GACTGTGCCTTCTAGTTGCCAGCCATCTGTTGTTTGCCCCTCCC
     CTGACACGGAAGATCAACGGTCGGTAGACAACAAACGGGGAGGG
1849 CCGTGCCTTCCTTGACCCTGGAAGGTGCCACTCCCACTGTCCTT
     GGCACGGAAGGAACTGGGACCTTCCACGGTGAGGGTGACAGGAA
1893 TCCTAATAAAATGAGGAAATTGCATCGCATTGTCTGAGTAGGTG
     AGGATTATTTTACTCCTTTAACGTAGCGTAACAGACTCATCCAC
1937 TCATTCTATTCTGGGGGGTGGGGTGGGGCAGGACAGCAAGGGGG
     AGTAAGATAAGACCCCCCACCCCACCCCGTCCTGTCGTTCCCCC
```

FIGURE 9C

1981 AGGATTGGGAAGACAATAGCAGGCATGCTGGGGATGCGGTGGGC
     TCCTAACCCTTCTGTTATCGTCCGTACGACCCCTACGCCACCCG
                                      BamHI    EcoRI
2025 TCTATGGAACCAGCTGGGGCTCGAGGGGGGATCCCCGGGAATTC
     AGATACCTTGGTCGACCCCGAGCTCCCCCCTAGGGGCCCTTAAG
2069 TGTGGAATGTGTGTCAGTTAGGGTGTGGAAAGTCCCCAGGCTCC
     ACACCTTACACACAGTCAATCCCACACCTTTCAGGGGTCCGAGG
2113 CCAGCAGGCAGAAGTATGCAAAGCATGCATCTCAATTAGTCAGC
     GGTCGTCCGTCTTCATACGTTTCGTACGTAGAGTTAATCAGTCG
2157 AACCAGGTGTGGAAAGTCCCCAGGCTCCCCAGCAGGCAGAAGTA
     TTGGTCCACACCTTTCAGGGGTCCGAGGGGTCGTCCGTCTTCAT
2201 TGCAAAGCATGCATCTCAATTAGTCAGCAACCATAGTCCCGCCC
     ACGTTTCGTACGTAGAGTTAATCAGTCGTTGGTATCAGGGCGGG
2245 CTAACTCCGCCCATCCCGCCCCTAACTCCGCCCAGTTCCGCCCA
     GATTGAGGCGGGTAGGGCGGGGATTGAGGCGGGTCAAGGCGGGT
                   StyI
2289 TTCTCCGCCCCATGGCTGACTAATTTTTTTATTTATGCAGAGG
     AAGAGGCGGGGTACCGACTGATTAAAAAAAATAAATACGTCTCC
2333 CCGAGGCCGCCTCGGCCTCTGAGCTATTCCAGAAGTAGTGAGGA
     GGCTCCGGCGGAGCCGGAGACTCGATAAGGTCTTCATCACTCCT
                 StyI
2377 GGCTTTTTTGGAGGCCTAGGCTTTTGCAAAAAGCTCCCGGGAGC
     CCGAAAAAACCTCCGGATCCGAAAACGTTTTTCGAGGGCCCTCG
2421 TTGGATATCCATTTTCGGATCTGATCAAGAGACAGGATGAGGAT
     AACCTATAGGTAAAAGCCTAGACTAGTTCTCTGTCCTACTCCTA
2465 CGTTTCGCATGATTGAACAAGATGGATTGCACGCAGGTTCTCCG
     GCAAAGCGTACTAACTTGTTCTACCTAACGTGCGTCCAAGAGGC
2509 GCCGCTTGGGTGGAGAGGCTATTCGGCTATGACTGGGCACAACA
     CGGCGAACCCACCTCTCCGATAAGCCGATACTGACCCGTGTTGT
2553 GACAATCGGCTGCTCTGATGCCGCCGTGTTCCGGCTGTCAGCGC
     CTGTTAGCCGACGAGACTACGGCGGCACAAGGCCGACAGTCGCG
2597 AGGGGCGCCCGGTTCTTTTTGTCAAGACCGACCTGTCCGGTGCC
     TCCCCGCGGGCCAAGAAAAACAGTTCTGGCTGGACAGGCCACGG
2641 CTGAATGAACTGCAGGACGAGGCAGCGCGGCTATCGTGGCTGGC
     GACTTACTTGACGTCCTGCTCCGTCGCGCCGATAGCACCGACCG

FIGURE 9 D

```
2685 CACGACGGGCGTTCCTTGCGCAGCTGTGCTCGACGTTGTCACTG
     GTGCTGCCCGCAAGGAACGCGTCGACACGAGCTGCAACAGTGAC
2729 AAGCGGGAAGGGACTGGCTGCTATTGGGCGAAGTGCCGGGGCAG
     TTCGCCCTTCCCTGACCGACGATAACCCGCTTCACGGCCCCGTC
2773 GATCTCCTGTCATCTCACCTTGCTCCTGCCGAGAAAGTATCCAT
     CTAGAGGACAGTAGAGTGGAACGAGGACGGCTCTTTCATAGGTA
2817 CATGGCTGATGCAATGCGGCGGCTGCATACGCTTGATCCGGCTA
     GTACCGACTACGTTACGCCGCCGACGTATGCGAACTAGGCCGAT
2861 CCTGCCCATTCGACCACCAAGCGAAACATCGCATCGAGCGAGCA
     GGACGGGTAAGCTGGTGGTTCGCTTTGTAGCGTAGCTCGCTCGT
2905 CGTACTCGGATGGAAGCCGGTCTTGTCGATCAGGATGATCTGGA
     GCATGAGCCTACCTTCGGCCAGAACAGCTAGTCCTACTAGACCT
2949 CGAAGAGCATCAGGGGCTCGCGCCAGCCGAACTGTTCGCCAGGC
     GCTTCTCGTAGTCCCCGAGCGCGGTCGGCTTGACAAGCGGTCCG
                                              StyI
2993 TCAAGGCGCGCATGCCCGACGGCGAGGATCTCGTCGTGACCCAT
     AGTTCCGCGCGTACGGGCTGCCGCTCCTAGAGCAGCACTGGGTA
3037 GGCGATGCCTGCTTGCCGAATATCATGGTGGAAAATGGCCGCTT
     CCGCTACGGACGAACGGCTTATAGTACCACCTTTTACCGGCGAA
3081 TTCTGGATTCATCGACTGTGGCCGGCTGGGTGTGGCGGACCGCT
     AAGACCTAAGTAGCTGACACCGGCCGACCCACACCGCCTGGCGA
3125 ATCAGGACATAGCGTTGGCTACCCGTGATATTGCTGAAGAGCTT
     TAGTCCTGTATCGCAACCGATGGGCACTATAACGACTTCTCGAA
3169 GGCGGCGAATGGGCTGACCGCTTCCTCGTGCTTTACGGTATCGC
     CCGCCGCTTACCCGACTGGCGAAGGAGCACGAAATGCCATAGCG
3213 CGCTCCCGATTCGCAGCGCATCGCCTTCTATCGCCTTCTTGACG
     GCGAGGGCTAAGCGTCGCGTAGCGGAAGATAGCGGAAGAACTGC
3257 AGTTCTTCTGAGCGGGACTCTGGGGTTCGAAATGACCGACCAAG
     TCAAGAAGACTCGCCCTGAGACCCCAAGCTTTACTGGCTGGTTC
3301 CGACGCCCAACCTGCCATCACGAGATTTCGATTCCACCGCCGCC
     GCTGCGGGTTGGACGGTAGTGCTCTAAAGCTAAGGTGGCGGCGG
3345 TTCTATGAAAGGTTGGGCTTCGGAATCGTTTTCCGGGACGCCGG
     AAGATACTTTCCAACCCGAAGCCTTAGCAAAAGGCCCTGCGGCC
3389 CTGGATGATCCTCCAGCGCGGGGATCTCATGCTGGAGTTCTTCG
     GACCTACTAGGAGGTCGCGCCCCTAGAGTACGACCTCAAGAAGC
```

FIGURE 9E

```
3433 CCCACCCCAACTTGTTTATTGCAGCTTATAATGGTTACAAATAA
     GGGTGGGGTTGAACAAATAACGTCGAATATTACCAATGTTTATT
3477 AGCAATAGCATCACAAATTTCACAAATAAAGCATTTTTTTCACT
     TCGTTATCGTAGTGTTTAAAGTGTTTATTTCGTAAAAAAAGTGA
3521 GCATTCTAGTTGTGGTTTGTCCAAACTCATCAATGTATCTTATC
     CGTAAGATCAACACCAAACAGGTTTGAGTAGTTACATAGAATAG
                BamHI
3565 ATGTCTGGATCCCGTCGACCTCGAGAGCTTGGCGTAATCATGGT
     TACAGACCTAGGGCAGCTGGAGCTCTCGAACCGCATTAGTACCA
3609 CATAGCTGTTTCCTGTGTGAAATTGTTATCCGCTCACAATTCCA
     GTATCGACAAAGGACACACTTTAACAATAGGCGAGTGTTAAGGT
3653 CACAACATACGAGCCGGAAGCATAAAGTGTAAAGCCTGGGGTGC
     GTGTTGTATGCTCGGCCTTCGTATTTCACATTTCGGACCCCACG
3697 CTAATGAGTGAGCTAACTCACATTAATTGCGTTGCGCTCACTGC
     GATTACTCACTCGATTGAGTGTAATTAACGCAACGCGAGTGACG
3741 CCGCTTTCCAGTCGGGAAACCTGTCGTGCCAGCTGCATTAATGA
     GGCGAAAGGTCAGCCCTTTGGACAGCACGGTCGACGTAATTACT
3785 ATCGGCCAACGCGCGGGGAGAGGCGGTTTGCGTATTGGGCGCTC
     TAGCCGGTTGCGCGCCCCTCTCCGCCAAACGCATAACCCGCGAG
3829 TTCCGCTTCCTCGCTCACTGACTCGCTGCGCTCGGTCGTTCGGC
     AAGGCGAAGGAGCGAGTGACTGAGCGACGCGAGCCAGCAAGCCG
3873 TGCGGCGAGCGGTATCAGCTCACTCAAAGGCGGTAATACGGTTA
     ACGCCGCTCGCCATAGTCGAGTGAGTTTCCGCCATTATGCCAAT
                                              AflIII
3917 TCCACAGAATCAGGGGATAACGCAGGAAAGAACATGTGAGCAAA
     AGGTGTCTTAGTCCCCTATTGCGTCCTTTCTTGTACACTCGTTT
3961 AGGCCAGCAAAAGGCCAGGAACCGTAAAAAGGCCGCGTTGCTGG
     TCCGGTCGTTTTCCGGTCCTTGGCATTTTTCCGGCGCAACGACC
4005 CGTTTTTCCATAGGCTCCGCCCCCCTGACGAGCATCACAAAAAT
     GCAAAAAGGTATCCGAGGCGGGGGGACTGCTCGTAGTGTTTTTA
4049 CGACGCTCAAGTCAGAGGTGGCGAAACCCGACAGGACTATAAAG
     GCTGCGAGTTCAGTCTCCACCGCTTTGGGCTGTCCTGATATTTC
4093 ATACCAGGCGTTTCCCCCTGGAAGCTCCCTCGTGCGCTCTCCTG
     TATGGTCCGCAAAGGGGGACCTTCGAGGGAGCACGCGAGAGGAC
```

FIGURE 9F

```
4137 TTCCGACCCTGCCGCTTACCGGATACCTGTCCGCCTTTCTCCCT
     AAGGCTGGGACGGCGAATGGCCTATGGACAGGCGGAAAGAGGGA
4181 TCGGGAAGCGTGGCGCTTTCTCAATGCTCACGCTGTAGGTATCT
     AGCCCTTCGCACCGCGAAAGAGTTACGAGTGCGACATCCATAGA
4225 CAGTTCGGTGTAGGTCGTTCGCTCCAAGCTGGGCTGTGTGCACG
     GTCAAGCCACATCCAGCAAGCGAGGTTCGACCCGACACACGTGC
4269 AACCCCCGTTCAGCCCGACCGCTGCGCCTTATCCGGTAACTAT
     TTGGGGGGCAAGTCGGGCTGGCGACGCGGAATAGGCCATTGATA
4313 CGTCTTGAGTCCAACCCGGTAAGACACGACTTATCGCCACTGGC
     GCAGAACTCAGGTTGGGCCATTCTGTGCTGAATAGCGGTGACCG
4357 AGCAGCCACTGGTAACAGGATTAGCAGAGCGAGGTATGTAGGCG
     TCGTCGGTGACCATTGTCCTAATCGTCTCGCTCCATACATCCGC
4401 GTGCTACAGAGTTCTTGAAGTGGTGGCCTAACTACGGCTACACT
     CACGATGTCTCAAGAACTTCACCACCGGATTGATGCCGATGTGA
4445 AGAAGGACAGTATTTGGTATCTGCGCTCTGCTGAAGCCAGTTAC
     TCTTCCTGTCATAAACCATAGACGCGAGACGACTTCGGTCAATG
4489 CTTCGGAAAAAGAGTTGGTAGCTCTTGATCCGGCAAACAAACCA
     GAAGCCTTTTCTCAACCATCGAGAACTAGGCCGTTTGTTTGGT
4533 CCGCTGGTAGCGGTGGTTTTTTTGTTTGCAAGCAGCAGATTACG
     GGCGACCATCGCCACCAAAAAAACAAACGTTCGTCGTCTAATGC
4577 CGCAGAAAAAAAGGATCTCAAGAAGATCCTTTGATCTTTTCTAC
     GCGTCTTTTTTTCCTAGAGTTCTTCTAGGAAACTAGAAAAGATG
4621 GGGGTCTGACGCTCAGTGGAACGAAAACTCACGTTAAGGGATTT
     CCCCAGACTGCGAGTCACCTTGCTTTTGAGTGCAATTCCCTAAA
4665 TGGTCATGAGATTATCAAAAAGGATCTTCACCTAGATCCTTTTA
     ACCAGTACTCTAATAGTTTTTCCTAGAAGTGGATCTAGGAAAAT
4709 AATTAAAAATGAAGTTTTAAATCAATCTAAAGTATATATGAGTA
     TTAATTTTTACTTCAAAATTTAGTTAGATTTCATATATACTCAT
4753 AACTTGGTCTGACAGTTACCAATGCTTAATCAGTGAGGCACCTA
     TTGAACCAGACTGTCAATGGTTACGAATTAGTCACTCCGTGGAT
4797 TCTCAGCGATCTGTCTATTTCGTTCATCCATAGTTGCCTGACTC
     AGAGTCGCTAGACAGATAAAGCAAGTAGGTATCAACGGACTGAG
4841 CCCGTCGTGTAGATAACTACGATACGGGAGGGCTTACCATCTGG
     GGGCAGCACATCTATTGATGCTATGCCCTCCCGAATGGTAGACC
```

FIGURE 9G

```
4885 CCCCAGTGCTGCAATGATACCGCGAGACCCACGCTCACCGGCTC
     GGGGTCACGACGTTACTATGGCGCTCTGGGTGCGAGTGGCCGAG
4929 CAGATTTATCAGCAATAAACCAGCCAGCCGGAAGGGCCGAGCGC
     GTCTAAATAGTCGTTATTTGGTCGGTCGGCCTTCCCGGCTCGCG
4973 AGAAGTGGTCCTGCAACTTTATCCGCCTCCATCCAGTCTATTAA
     TCTTCACCAGGACGTTGAAATAGGCGGAGGTAGGTCAGATAATT
5017 TTGTTGCCGGGAAGCTAGAGTAAGTAGTTCGCCAGTTAATAGTT
     AACAACGGCCCTTCGATCTCATTCATCAAGCGGTCAATTATCAA
5061 TGCGCAACGTTGTTGCCATTGCTACAGGCATCGTGGTGTCACGC
     ACGCGTTGCAACAACGGTAACGATGTCCGTAGCACCACAGTGCG
5105 TCGTCGTTTGGTATGGCTTCATTCAGCTCCGGTTCCCAACGATC
     AGCAGCAAACCATACCGAAGTAAGTCGAGGCCAAGGGTTGCTAG
5149 AAGGCGAGTTACATGATCCCCCATGTTGTGCAAAAAAGCGGTTA
     TTCCGCTCAATGTACTAGGGGGTACAACACGTTTTTTCGCCAAT
5193 GCTCCTTCGGTCCTCCGATCGTTGTCAGAAGTAAGTTGGCCGCA
     CGAGGAAGCCAGGAGGCTAGCAACAGTCTTCATTCAACCGGCGT
5237 GTGTTATCACTCATGGTTATGGCAGCACTGCATAATTCTCTTAC
     CACAATAGTGAGTACCAATACCGTCGTGACGTATTAAGAGAATG
5281 TGTCATGCCATCCGTAAGATGCTTTTCTGTGACTGGTGAGTACT
     ACAGTACGGTAGGCATTCTACGAAAAGACACTGACCACTCATGA
5325 CAACCAAGTCATTCTGAGAATAGTGTATGCGGCGACCGAGTTGC
     GTTGGTTCAGTAAGACTCTTATCACATACGCCGCTGGCTCAACG
5369 TCTTGCCCGGCGTCAATACGGGATAATACCGCGCCACATAGCAG
     AGAACGGGCCGCAGTTATGCCCTATTATGGCGCGGTGTATCGTC
5413 AACTTTAAAAGTGCTCATCATTGGAAAACGTTCTTCGGGGCGAA
     TTGAAATTTTCACGAGTAGTAACCTTTTGCAAGAAGCCCCGCTT
5457 AACTCTCAAGGATCTTACCGCTGTTGAGATCCAGTTCGATGTAA
     TTGAGAGTTCCTAGAATGGCGACAACTCTAGGTCAAGCTACATT
5501 CCCACTCGTGCACCCAACTGATCTTCAGCATCTTTTACTTTCAC
     GGGTGAGCACGTGGGTTGACTAGAAGTCGTAGAAAATGAAAGTG
5545 CAGCGTTTCTGGGTGAGCAAAAACAGGAAGGCAAAATGCCGCAA
     GTCGCAAAGACCCACTCGTTTTTGTCCTTCCGTTTTACGGCGTT
5589 AAAAGGGAATAAGGGCGACACGGAAATGTTGAATACTCATACTC
     TTTTCCCTTATTCCCGCTGTGCCTTTACAACTTATGAGTATGAG
```

FIGURE 9H

```
5633 TTCCTTTTTCAATATTATTGAAGCATTTATCAGGGTTATTGTCT
     AAGGAAAAAGTTATAATAACTTCGTAAATAGTCCCAATAACAGA
5677 CATGAGCGGATACATATTTGAATGTATTTAGAAAAATAAACAAA
     GTACTCGCCTATGTATAAACTTACATAAATCTTTTATTTGTTT
5721 TAGGGGTTCCGCGCACATTTCCCCGAAAAG
     ATCCCCAAGGCGCGTGTAAAGGGGCTTTTC
```

FIGURE 9 I

OPEN READING FRAME ANALYSIS

DNA> pRLD3D4.DI starts at nt #: +665
number of amino acids: 361
molecular weight: 38821

Three letter representation:
-24 met-arg-pro-ser-gly-thr-ala-gly-ala-ala-
leu-leu-ala-leu-leu-ala-ala-leu-cys-pro-
$\quad\quad\quad\quad\quad$ +1
ala-ser-arg-ala-leu-glu-glu-lys-lys-val-
$\quad\quad$ +8  +297
cys-gln-asp-gly-val-arg-lys-cys-lys-lys-
cys-glu-gly-pro-cys-arg-lys-val-cys-asn-
gly-ile-gly-ile-gly-glu-phe-lys-asp-ser-
leu-ser-ile-asn-ala-thr-asn-ile-lys-his-
phe-lys-asn-cys-thr-ser-ile-ser-gly-asp-
leu-his-ile-leu-pro-val-ala-phe-arg-gly-
asp-ser-phe-thr-his-thr-pro-pro-leu-asp-
pro-gln-glu-leu-asp-ile-leu-lys-thr-val-
lys-glu-ile-thr-gly-phe-leu-leu-ile-gln-
ala-trp-pro-glu-asn-arg-thr-asp-leu-his-
ala-phe-glu-asn-leu-glu-ile-ile-arg-gly-
arg-thr-lys-gln-his-gly-gln-phe-ser-leu-
ala-val-val-ser-leu-asn-ile-thr-ser-leu-
gly-leu-arg-ser-leu-lys-glu-ile-ser-asp-
gly-asp-val-ile-ile-ser-gly-asn-lys-asn-
leu-cys-tyr-ala-asn-thr-ile-asn-trp-lys-
lys-leu-phe-gly-thr-ser-gly-gln-lys-thr-
lys-ile-ile-ser-asn-arg-gly-glu-asn-ser-
cys-lys-ala-thr-gly-gln-val-cys-his-ala-
leu-cys-ser-pro-glu-gly-cys-trp-gly-pro-

FIGURE 10 glu-pro-lys-asp-cys-val-ser-cys-arg-asn-
val-ser-arg-gly-arg-glu-cys-val-asp-lys-
cys-asn-leu-leu-glu-gly-glu-pro-arg-glu-
phe-val-glu-asn-ser-glu-cys-ile-gln-cys-
his-pro-glu-cys-leu-pro-gln-ala-met-asn-
ile-thr-cys-thr-gly-arg-gly-pro-asp-asn-
cys-ile-gln-cys-ala-his-tyr-ile-asp-gly-
pro-his-cys-val-lys-thr-cys-pro-ala-gly-
val-met-gly-glu-asn-asn-thr-leu-val-trp-
lys-tyr-ala-asp-ala-gly-his-val-cys-his-
leu-cys-his-pro-asn-cys-thr-tyr-gly-cys-
thr-gly-pro-gly-leu-glu-gly-cys-pro-thr-
asn-gly-pro-lys-ile-pro-ser-ile-ala-thr-
gly-STOP
625

FIGURE 10

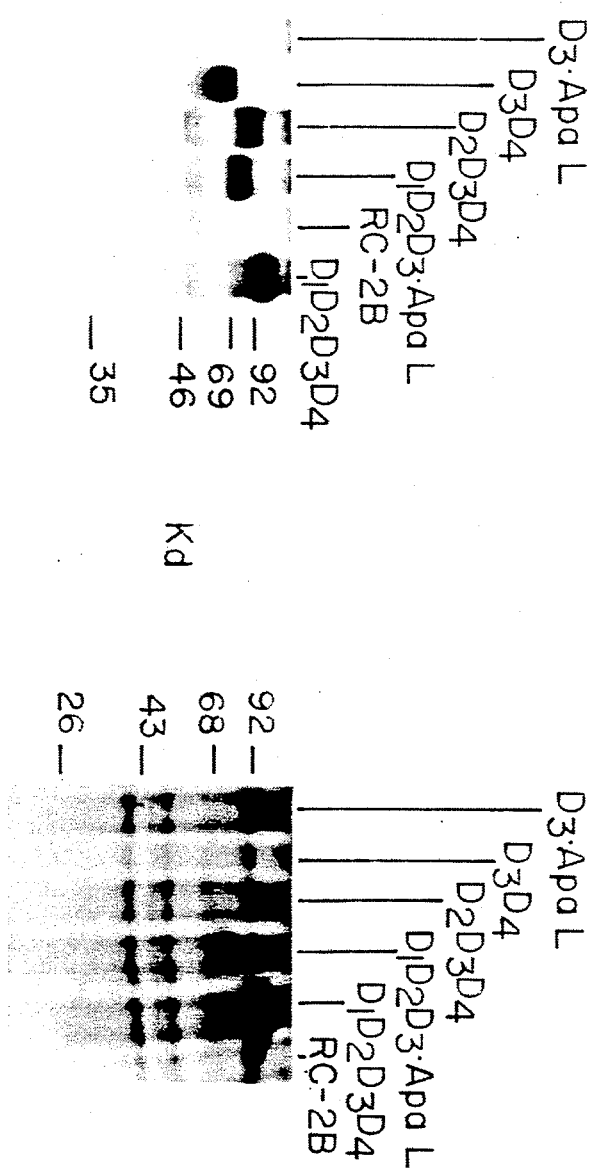

EGF RECEPTOR TRUNCATES

This is a continuation-in-part of U.S. application Ser. No. 07/536,896 filed Jun. 12, 1990, abandoned.

BACKGROUND OF INVENTION

1. Field of the Invention

The Epidermal Growth Factor Receptor (hereinafter the EGF receptor) is known to be a 170,000 dalton glycoprotein (Reference No. 1) present on the surface of a variety of cell types. A gene for this receptor can be obtained by a process described in U.S. Pat. No. 4,933,294 (Reference No. 2) which is incorporated herein for this purpose. Like other known cell surface receptors, it has an extracellular and cytoplasmic (or intracellular) domain wherein the extracellular domain is capable of binding a substance so that the cytoplasmic domain interacts with another cellular molecule. That is, the interaction between the cytoplasmic domain of the EGF receptor with another cellular molecule is a function of the binding by the substance to the extracellular domain of the EGF receptor. The substance that binds the receptor is known as a ligand. Thus, the term "ligand" is limited only by an ability to affect the extracellular portion of the receptor so that the cytoplasmic domain is caused to interact with another molecule inside the cell. This interaction is termed "signal transduction".

For example, the signal transducing function of epidermal growth factor to the EGF receptor results in tyrosine phosphorylation and initiates a cascade of events that culminate in cell division essential to the growth and reproduction of the cell (Reference No. 3).

The cascade of events may be initiated by conformational changes of the receptor or receptor-receptor interactions effected by the ligand which modifies the affect of the receptor on cytoplasmic components.

The term ligand does not imply any particular molecular size or other structural or compositional feature. Furthermore, ligands may be natural or non-natural.

In an effort to find better techniques to design drugs, generally substances having low molecular weight, the research of the pharmaceutical industry is focusing on receptor technology and more specifically on ligands which bind to the receptor.

Conversely, the receptor truncates of the present invention are substances which bind ligands that offend an organism by binding the extracellular portion of an EGF receptor. Adsorptive capacities of the truncates may provide a benefit to an organism against detrimental invasion by an offending substance such as a virus or excess epidermal growth factor receptor ligand.

The present invention provides parts of the EGF receptor to which ligands bind for ligands that bind the EGF receptor itself. The parts are a glycoprotein having selected EGF receptor sequences preferably having substantially fewer amino acids than the EGF receptor itself such that the glycoprotein is relative low molecular weight. In other words, the glycoproteins of the present invention bind ligands of the EGF receptor, but are preferably smaller than an EGF receptor and are soluble proteins and as so may bind a natural ligand without transmitting a signal for the growth and reproduction of a cell.

Among the known natural ligands which bind specifically to the EGF receptor and initiate a cellular growth response are: Epidermal Growth Factor, Transforming Growth Factor $\alpha$ (Reference No. 4) Amphiregulin (Reference No. 5), and Vaccinia Growth Factor (Reference No. 6.)

Thus, the present invention is portions of the extracellular domain of the EGF receptor which are produced using recombinant DNA methods to yield soluble proteins capable of binding the natural ligands.

2. Description of the Prior Art

The extracellular domain of the EGF receptor is described as an external EGF binding domain comprising 621 amino acids (Reference No. 7). On the basis of amino acid sequence analysis, this extracellular region of EGF receptor can be divided into four domains. It has been suggested that the extracellular portion of the EGF receptor which is flanked by two cysteine-rich domains contributes most of the interactions that define ligand-binding specificity of the EGF receptor (Reference No. 8). The four domains are identified as $D_1$, $D_2$, $D_3$, and $D_4$.

The portion of the EGF receptor defining ligand binding for the receptor is said to be the $D_3$ domain within the EGF receptor.

The present invention provides an expressed protein which is the $D_3$ domain. This protein and additional proteins of the present invention define an independent portion of the EGF receptor which is a properly folded protein capable of ligand binding. Such a protein, that is only a portion of the whole EGF receptor, is not previously described.

The present invention may use either an EGF receptor cDNA sequence (Reference No. 1) or the EGF receptor gene (Reference No. 9) and their expression which are obtained and carried out respectively by conventional methods.

SUMMARY OF THE INVENTION

The present invention is a novel protein having selected amino acid sequences of the EGF receptor. These sequences are meant to include functional equivalents of amino acids present in the sequences.

Additionally, the present invention embodies any DNA sequence coding for the novel proteins presented in FIGS. 4, 7, and 10.

These may be 'mini-genes'. The 'mini-genes' are cDNA sequences coding for the desired protein which is flanked by a promotor on the 5' side of the sequence and a polyadenylation region on the 3' side of the cDNA. The cDNA sequences are as disclosed or are also meant to extend to functional equivalents thereof.

These proteins may also be prepared through the use of the genomic DNA sequence encoding the EGF receptor.

Thus, the present invention is also a process for the preparation of the selected amino acid sequences of the EGF receptor.

The amino acid sequences are set out in accordance with the three-letter abbreviations of 37 CFR 1.822(b)(2) and the truncate codes are set out in accordance with the base codes of 37 CFR 1.822(b)(1).

BRIEF DESCRIPTION OF THE DRAWINGS

FIG. 3 shows the DNA sequence of the pRLD$_1$D$_2$D$_3$.ApaL construct as described in the Experimental Section.

FIG. 4 presents the amino acid sequence of the LD$_1$D$_2$D$_3$.ApaL protein, deduced from the DNA sequence shown in FIG. 3.

FIG. 5 represents the plasmid map of pRLD$_2$D$_3$D$_4$ which notes the location of the EGF leader, $D_2$, $D_3$, and $D_4$. domains of EGF receptor gene.

FIG. 6 shows the DNA sequence of the pRLD$_2$D$_3$D$_4$ construct as described in the Experimental Section.

FIG. 7 presents the amino acid sequence of the LD$_2$D$_3$D$_4$ protein, deduced from the DNA sequence shown in FIG. 6.

FIG. 9 shows the DNA sequence of the pRLD$_3$D$_4$ construct as described in the Experimental Section.

FIG. 10 presents the amino acid sequence of the LD$_3$D$_4$ protein deduced from the DNA sequence shown in FIG. 9.

FIG. 11 (a and b) shows a radiograph of SDS-Polyacrylamide gel electrophoresis analysis of immunoprecipitates from the $^{35}$S labeled supernatants of Cos cells electroporated with the EGF receptor truncate genes as described in the Experimental Section. FIG. 11a depicts the immunoprecipitation with Ab-1 and FIG. 11b depicts the immunoprecipitation with RPN.513.

DETAILED DESCRIPTION OF INVENTION

Figure 1:
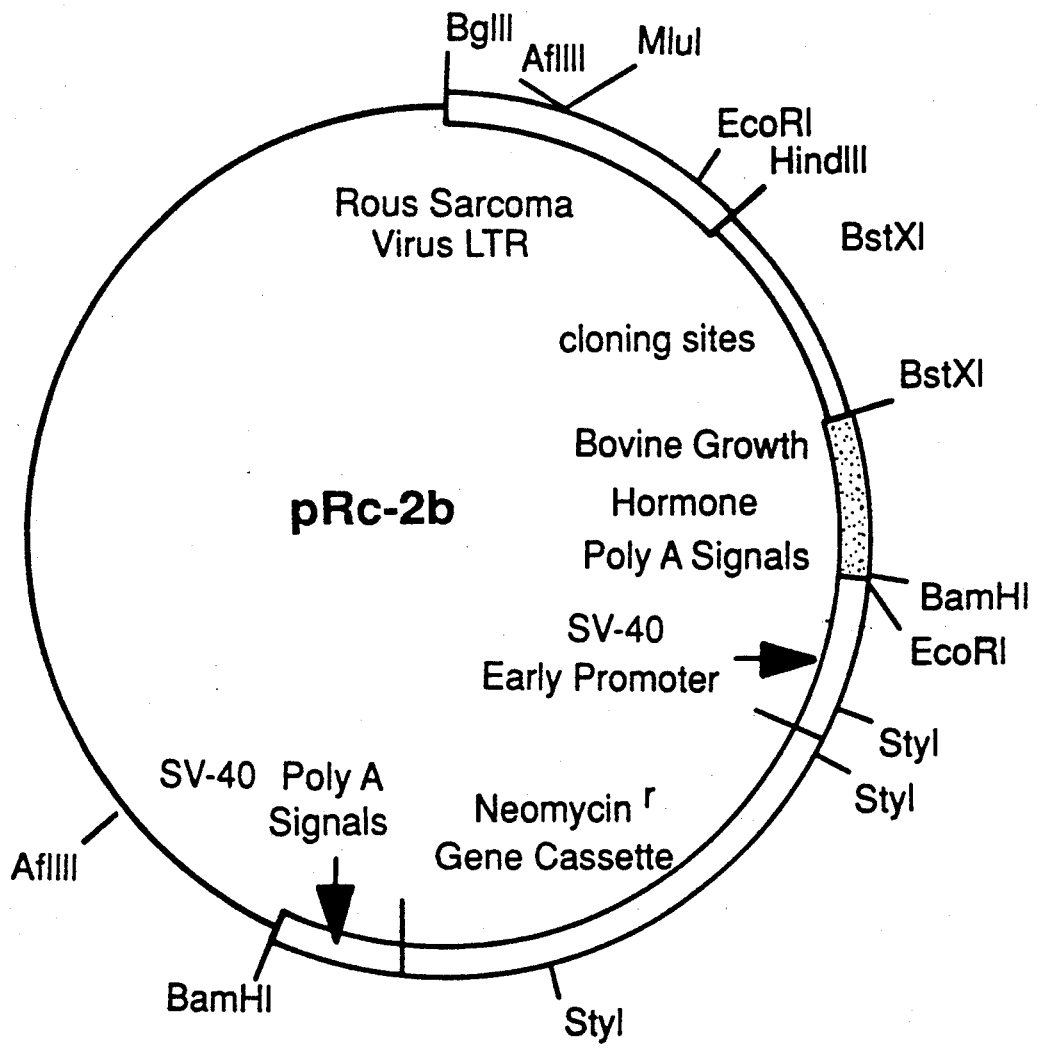
FIG. 1 represents the construction of plasmid RC-2b having NRRL No. B-18718 deposited Sep. 26, 1990, the mammalian expression vector used for the introduction of EGF receptor truncate 'mini-genes' into cells and is described in the Experimental Section hereinafter.

A glycoprotein having selected EGF receptor sequences but which is capable of binding ligands of an EGF receptor are produced in mammalian cells by recombinant DNA methodology. Selection of desired sequences may be limited only by the requirement that ligands which bind EGF receptor must also bind the desired sequences. Preferably, the sequences are a small single region of the receptor of about a 20kd polypeptide.

Additionally, although mammalian cells provide a host for the production of glycoproteins, the glycosylation sites which influence folding of such glycoproteins may be unnecessary for reasonable affinity (100 times less or better in EGF binding) compared to the EGF receptor. Thus, recombinant proteins produced by mammalian cell culture, yeast culture, bacterial culture, and the like recombinant DNA technology also may provide recombinant receptor proteins which can bind EGF or similar ligands.

'Mini-genes' coding for receptor truncates are readily adapted to high-level stable expression in Chinese Hamster ovary cells by insertion of a Dihydrofolate Reductase Gene Cassette into the vector having such mini-genes and by methotrexate induced gene amplification of transfected cells. In addition, any known or commercially available mammalian expression system including readily available plasmids, can be used. Alternatively, the DNA sequence coding (described herein) for the receptor truncates may be excised from the mammalian expression vector and placed into vectors to provide high level expression in yeast, bacterial or insect cell systems.

The mini-genes are preferably designed to produce secreted recombinant proteins from cells. Thus, it is preferred to construct 'mini-genes' coding for the desired protein and express these truncates transiently in Cos cells for analysis. Such proteins may be metabolically labeled with $^{35}$S-methionine and cysteine followed by analysis of truncate proteins present in the culture media by immunoprecipitation with various anti-sera or monoclonal antibodies.

Ligand binding is assessed by an EGF or αTGF affinity matrix.

The present invention is also a process for selection of desired sequences for the production of proteins which are portions of the EGF receptor having the capability of binding ligands by further truncation.

This selection process is designed to provide increasingly smaller portions of the EGF receptor which retain the binding capability. For example, further weak reactivity with anti-sera raised against native EGF receptors or monoclonal antibodies RPN.513 or Ab-1 indicated a small amount of properly folded receptor protein was obtained from LD$_3$.APAL and LD$_1$D$_2$D$_3$ constructs. Truncates containing fewer sequences than those required to express the D$_3$ protein in these documented truncates were found not to be expressed at high enough levels in mammalian cells to examine EGF binding. In like systems expressing like proteins, this indicates improper folding and rapid degradation in the cells. Alternate expression strategies can correct this problem. Thus, the present invention also includes LD$_3$.APAL.

Additionally, two truncates which code for the smaller portions of the EGF receptor are found to bind EGF (LD$_1$D$_2$D$_3$.APAL and LD$_3$D$_4$ described hereinafter) and these proteins have an overlapping sequence. However, it is found that expression of the overlapping sequence LD$_3$.APAL is greatly diminished, presumably because there is insufficient amino acid sequence necessary to adequately fold the D$_3$ EGF binding domain in Cos cells. The process of the present invention encompasses a previously unpredictable structural profile of the EGF receptor.

EXPERIMENTAL

The following examples are offered by way of illustration and not by way of limitation.

The construction of 'mini-genes' coding for three novel recombinant glycoproteins containing EGF receptor sequences and preliminary characterization of their protein products is described.

All DNA manipulations were done according to standard procedures. See *Molecular Cloning*, T. Maniatis et al., Cold Spring Harbor Lab., 1982. Enzymes used in cloning were obtained either from New England Biolabs or Bethesda Research Laboratories and employed according to the supplier's directions.

1. LD$_1$D$_2$D$_3$. ApaL. This EGF receptor truncate codes for a protein encompassing amino acids Met$_{-24}$ to Val$_{505}$ of the EGF receptor. Amino acid +1 designates the mature amino terminus of the receptor. The first step of this multiple step construction strategy is to insert a 1567 base pair (bp) Sacl-Apal fragment of the EGF receptor cDNA into Sacl-Eco R1 cleaved pSP-65

(Promega) with synthetic oligonucleotide linkers (shown as capital letters) as shown.

| | Apa I | | | | 1/2 Eco R1 |
|---|---|---|---|---|---|
| | ggc | cCC | TGA | CCAGCACAATGG | |
| ~g | | | | | |
| EGFR | | | | | |
| ~c | CCG | GGG | ACT | GGTCGTGTTACCTTAA | |
| | Gly | Pro | STOP | Bst X1 | |
| | 493 | 494 | | | |

Figure 2:
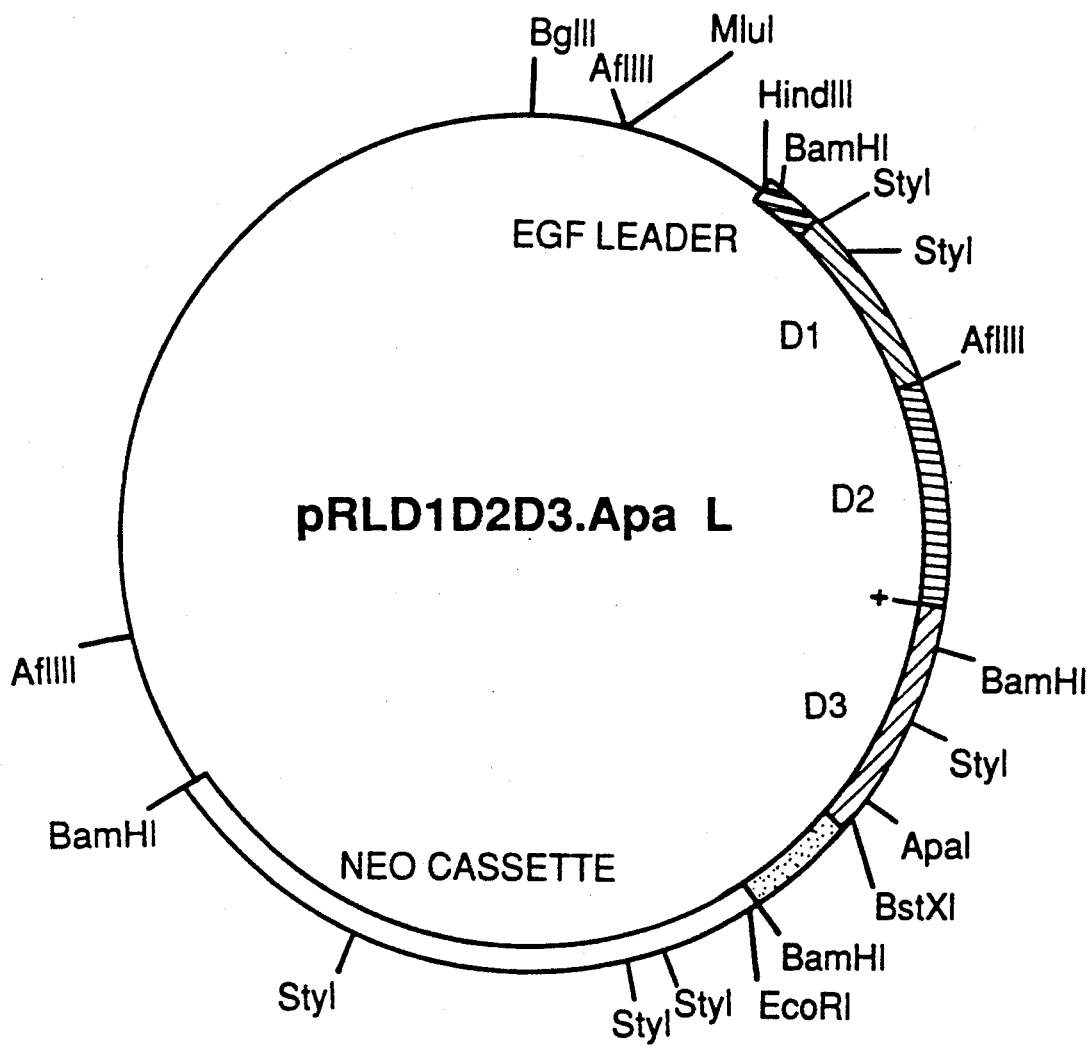
FIG. 2 represents the plasmid map of pRLD$_1$D$_2$D$_3$.ApaL which notes the location of the EGF leader, $D_1$, $D_2$, and $D_3$ domains of the EGF receptor gene and ApaL region inserted into the RC-2b expression plasmid as described in the Experimental Section.

This step introduces a stop codon after amino acid 494 of the receptor and creates a Hind 3 site 5' of the receptor coding sequence (from the pSP.6S polylinker) and a Bst X1 site 3' of the coding sequence. This construct is designated pSLD$_1$D$_2$D$_3$. The 1623 bp. Hind 3-Bst X1 EGF receptor fragment of pSLD$_1$D$_2$D$_3$ is inserted into Hind 3+Bst X1 cleaved RC-2b mammalian expression vector (FIG. 1). This resultant plasmid, pRLD$_1$D$_2$D$_3$ is further modified by inserting the indicated oligonucleotide linkers into Apal+ Bst X1 cut pRLD$_1$D$_2$D$_3$ resulting in the construction of pRLD$_1$D$_2$D$_3$.Apa L. Restriction site mapping and DNA sequencing confirms that this construct is as designed. The plasmid map and DNA sequence of pRLD$_1$D$_2$D$_3$.Apa L is presented in FIGS. 2 and 3. The amino acid sequence of the LD$_1$D$_2$D$_3$.Apa L protein, deduced from DNA sequence, is presented in FIG. 4.

| | Apa 1 | | | | | | | | | | | | | 1/2 Bst X1 |
|---|---|---|---|---|---|---|---|---|---|---|---|---|---|---|
| ~g | ggc | cCC | GAG | CCC | AGG | GAC | TGC | GTC | TCT | TGC | CGG | AAT | GTC | TGA | TAAGCTTCCAGCACA |
| EGFR | | | | | | | | | | | | | | | |
| ~c | CCC | GGG | CTC | GGG | TCC | CTG | ACG | CAG | AGA | ACG | GCC | TTA | CAG | ACT | ATTCGAAGGTC |
| | Gly | Pro | Glu | Pro | Arg | Asp | Cys | Val | Ser | Cys | Arg | Asn | Val | STOP | |
| | 493 | | | | | | | | | | | | 505 | | |

2. LD$_2$D$_3$D$_4$. This EGF receptor truncate is designed to meld the EGF receptor leader sequence to the receptor protein beginning at Ser$_{150}$. This protein possesses the leader peptide (amino acids Met$_{-24}$ to Ala$_{-1}$), 9 amino acids of the mature amino terminus of the receptor (Leu$_1$ to Gly$_9$) and receptor sequences Ser$_{150}$ to Gly$_{625}$. In order to construct the gene for this protein a 1961 bp. Sacl-Bst X1 fragment encoding the entire EGF receptor extracellular domain is inserted into Sacl-Eco R1 cleaved pSP-65 with the oligonucleotide linkers as shown, resulting in the plasmid pSLD$_1$D$_2$D$_3$D$_4$.

| Bst X-1 | | | | Bst-X1 | |
|---|---|---|---|---|---|
| (destroyed) | | | | | 1/2Eco R1 |
| ~cc | act | ggg | TGA | CCAGCACAATGG | |
| D$_4$ | | | | | |
| ~gg | tgA | CCC | ACT | GGTCGTGTTACC TTAA | |
| | Thr | Gly | STOP | | |
| | 624 | 625 | | | |

A 1423 bp Af13-Bst X1 fragment of pSLD$_1$D$_2$D$_3$D$_4$ (coding for amino acids 150 to 625 of the receptor) is ligated to a 3107 bp Sty 1-Bst X1 fragment of pSLD$_1$D$_2$D$_3$ (contains DNA of pSP-65 vector, EGF receptor leader sequence and Leu$_1$ to Gly$_9$)with the linkers as shown, resulting in pSLD$_2$D$_3$D$_4$.

| c | CAA | GGC | AGC | AAc | atg | t |
|---|---|---|---|---|---|---|
| Leader | | | | | | D$_2$D$_3$D$_4$ |
| g | gtt | cCG | TCG | TTG | TAC | a |
| | Gln | Gly | Ser | Asn | Met | |
| | 8 | 9 | 150 | 151 | 152 | |

Transfer of this truncate gene from pSP-65 to RC-2b is accomplished by inserting the 1596 bp Hind3-Bst X1 fragment of pSLD$_2$D$_3$D$_4$ into Hind3+Bst X1 cleaved RC-2b resulting in pRLD$_2$D$_3$D$_4$. Restriction site mapping and DNA sequencing confirms that this construct is as designed. The plasmid map and DNA sequence for pRLD$_2$D$_3$D$_4$ is presented in FIGS. 5 and 6. The amino acid sequence of LD$_2$D$_3$D$_4$ deduced from the DNA sequence, is presented in FIG. 7.

3. LD$_3$D$_4$. This EGF receptor protein possesses the leader peptide (Met$_{-24}$ to Ala$_{-1}$), Leu$_1$ to Gln$_8$ of the mature amino terminus of the receptor and receptor sequence Asp$_{297}$ to Gly$_{625}$. To construct the gene for this protein a 587 bp Aha2-Bst X1 fragment of pRLD$_1$D$_2$D$_3$ (coding for amino acids Asp$_{297}$ to Pro$_{494}$) is ligated to the 3107 bp Styl-Bst X1 fragment of pSLD$_1$D$_2$D$_3$ with the oloigonucleotide linkers as shown.

| | 1/2 Sty 1 | | | |
|---|---|---|---|---|
| | (destroyed) | | | Aha II |
| ~c | CAA | GAT | GGc | gtc |
| EGFR Leader | | | | | D$_3$~ |
| ~g | gtt | cTA | CCG | Cac |
| | Gln | Asp | Gly | Val |
| | 8 | 297 | 298 | 299 |

Figure 8:
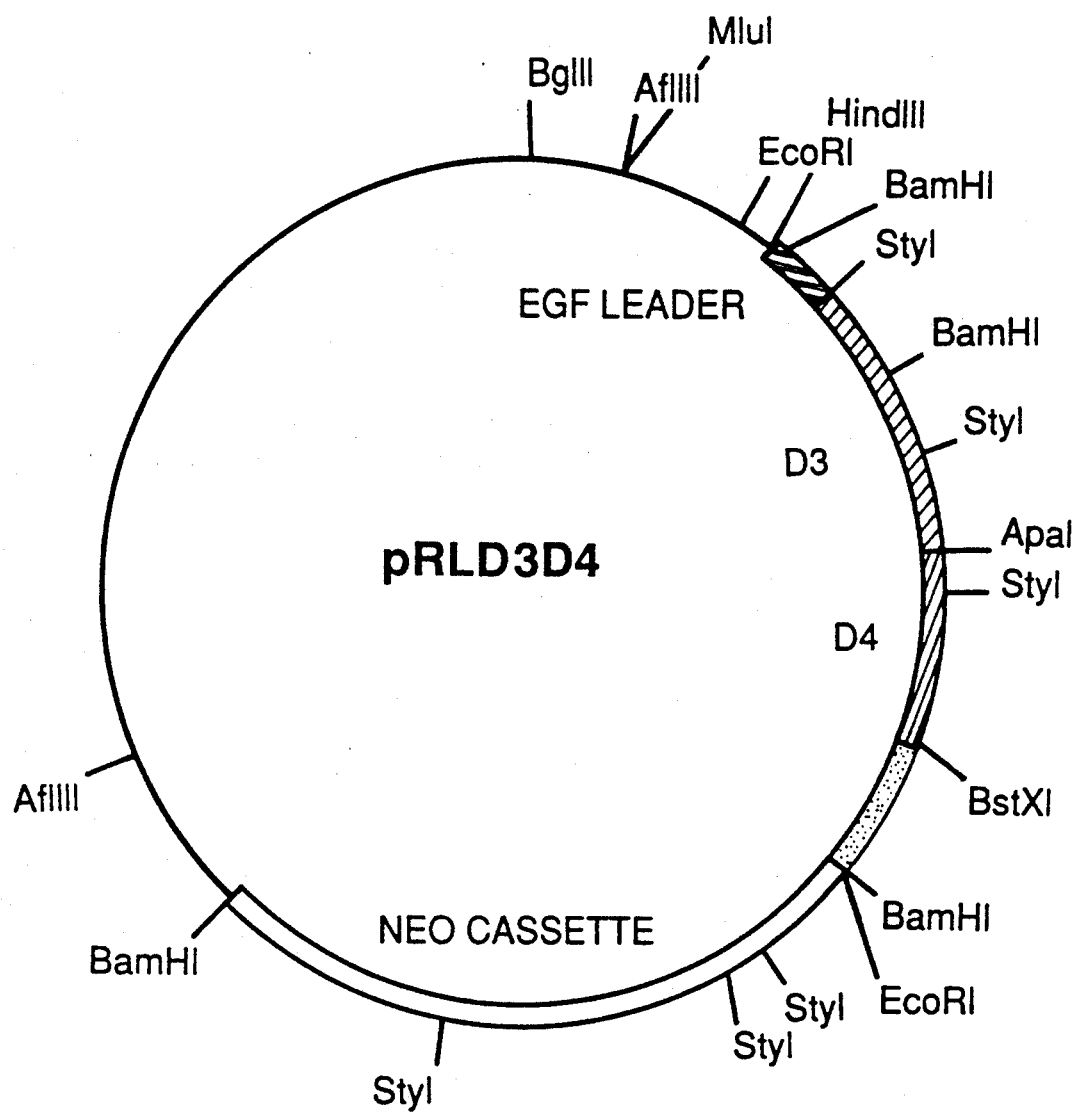
FIG. 8 represents the plasmid map pLRD$_3$D$_4$ which notes the location of the EGF leader, $D_3$ and $D_4$ domains of the EGF receptor gene, as described in the Experimental Section.

This plasmid, pSLD$_3$, is subsequently cleaved with Hind3+Bst X1 and the 758 bp fragment (encoding amino acids −24 to 494) is ligated to Hind3+Bst X1 cut RC-2b. This plasmid is designated pRLD$_3$. pRLD$_3$D$_4$ is constructed by inserting a 406 bp Apal-Bst X1 fragment from pRLD$_2$D$_3$D$_4$ into the 5357 bp Apal-BstX1 fragment of pRLD$_3$. Restriction site mapping and DNA sequencing confirms that this construct is as designed. The plasmid map and DNA sequence for pRLD$_3$D$_4$ is presented in FIGS. 8 and 9. The amino acid sequence of the LD$_3$D$_4$ protein, deduced from the DNA sequence is presented in FIG. 10.

Figure 12:
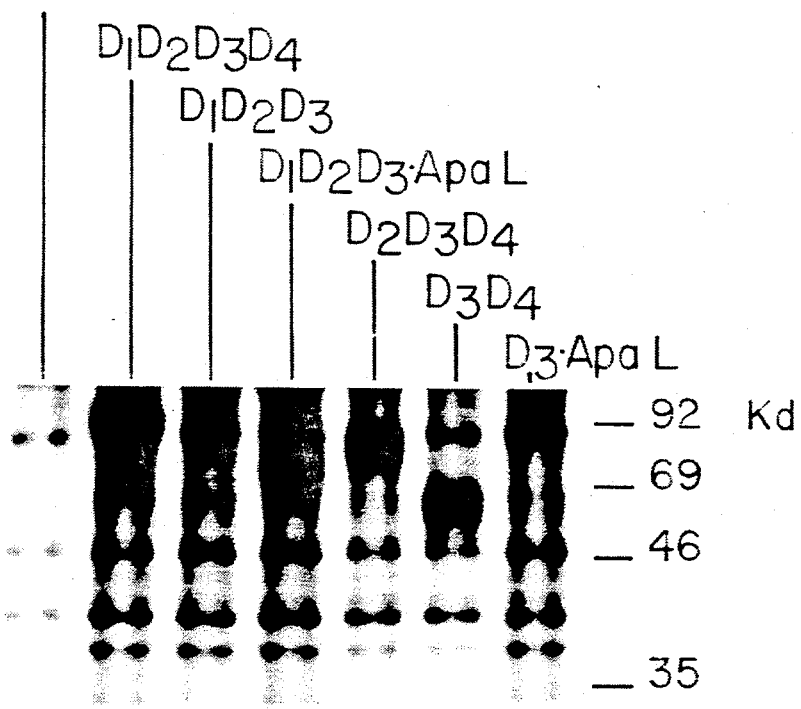
FIG. 12 shows an experiment similar to that described for FIG. 11 using an EGF-affi gel matrix as described in the Experimental Section.

Transient expression of these EGF receptor truncate proteins is accomplished by electroporation (Reference No. 11) of Cos 1 cells (Reference No. 12) at 3×10$^6$ cells/ml. with 20 ug. of CsCl purified (Reference No. 13) plasmid DNA using a BRL Cell-porator set at 330 uF, 300 volts at low Ohms. Following a 2 minute incubation at room temperature, the electroporated cells (0.3 ml.) are seeded in a 100 mm tissue culture plate containing 10 ml. of DMEM+10% Fetal Calf Serum. Forty eight hours after the electroporation the media is changed to labelling media consisting of RPMI (without Methioine and cysteine), 5% dialyzed fetal calf serum, 50 uCi/ml, each of $^{35}$S- Methioine and $^{35}$S- Cysteine and 50 ug/ml. gentamycin. After a 24 hour labelling period, the media is removed, Phenyl Methyl Sulphonyl Fluoride (a protease inhibitor) is added to 0.2 uM. and centrifuged at 10,000 rpm for 10 minutes at 4° C. The supernatant is removed and used for immunoprecipitation studies (Reference No. 13) with EGF receptor specific monoclonal antibodies Ab-1(Oncogene Science) and RPN.513 (Amersham Corp.). EGF binding abilities of these proteins is assessed by incubation with an EGF-affinity matrix prepared by crosslinking EGF with Affi-gel 10 (Biorad Laboratories). FIG. 11 (a and b) shows a radiograph of SDS-Polyacrylamide gel electrophoresis analysis of immunoprecipitates from the $^{35}$S labelled supernatants of Cos cells electroporated with the EGF receptor truncate genes. FIG. 11a depicts immunoprecipitation with Ab-1 and FIG. 11b uses RPN.513. This figure shows that a 68,000 dalton protein from cells electroporated with pRLD$_1$D$_2$D$_3$.Apa L is specifically precipitated with either of the monoclonal antibodies whereas 85,000 and 55,000 dalton proteins from cells electroporated with pRLD$_2$D$_3$D$_4$ or pRLD$_3$D$_4$ respectively are specifically precipitated with only the Ab-1 monoclonal. FIG. 12 shows a similar experiment using the EGF-affi gel matrix. This experiment indicates that the 3 receptor truncate proteins, LD$_1$D$_2$D$_3$.Apa L, LD$_2$D$_3$D$_4$ and LD$_3$D$_4$ bind the EGF matrix while cells electroporated with pRLD$_1$D$_2$D$_3$, LD$_3$.ApaL or RC-2b do not produce a protein capable of binding EGF.

The recombinant proteins described in the preceding section can be over-expressed in any of a number of heterologous cell systems including a Chinese Hamster Ovary system using Dihydrofolate Reductase co-amplification (Reference No. 14) or a Baculovirus insect cell system (Reference No. 15).

The purified proteins of the present invention, such as LD$_1$D$_2$D$_3$.Apa L, LD$_2$D$_3$D$_4$ and LD$_3$D$_4$ can be used as an adsorptive agent for any moieties that bind the EGF receptor, such as EGF, TGF-$\alpha$, and any as yet undiscovered peptides or etiological agents, such as a virus that uses the EGF receptor as the portal of entry to the cell. As an adsorptive agent these proteins will compete with the EGF receptor present on the cell surface for binding of the ligands and thereby inhibit the action of the ligands.

For example, it is accepted that epidermal growth factor binding induces a conformation change in the external domain of its receptor (Reference No. 9); thus, excess epidermal growth factor bound to the proteins of the present invention would prevent effects on an organism's endogenous EGF receptor by EGF binding. In like manner, recognition of EGF receptor's participation as a portal for infectivity for vaccinia virus is disclosed by N. H. Colburn et al. (Reference No. 16) so addition of the present proteins providing absorption of the virus may prevent entry into otherwise susceptible cells (Reference No. 17).

Of course, the EGF receptor truncate proteins of the present invention are also useful in any manner previously set out for use of EGF receptor itself. For example, the use described for the EGF receptor itself in a method for the detection of abnormalities in mammalian cell growth is described in U.S. Pat. No. 4,933,294 (Reference No. 2) which is therefor incorporated herein by reference.

Also, EGF receptor truncate proteins of the present invention are useful to prepare novel receptors for efficient determination of ligands and their antagonists or agonists as described in U.S. Pat. No. 4,859,609 (Reference No. 17) which is also incorporated by reference, therefor.

REFERENCES

1. A. Ullrich, L. Coussens, J. S. Hayflick, T. J. Dull, A. Gray, A. W. Tam, J. Lee, Y. Yarden, T. A. Libermann, J. Schlessinger, J. Downward, E. L. V. Mayes, N. Whittle, M. D. Waterfield, and P. H. Seeburg; "Human epidermal growth factor receptor cDNA sequence and aberrant expression of the amplified gene in A431 epidermoid carcinoma cells." Nature, Vol. 309, 418–425 (31 May 1984).
2. U.S. Pat. No. 4,933,294, M. D. Waterfield, et al. issued Jun. 12, 1990.
3. EMBO J., September 1986 5(9), p 2179–90.
4. Todaro, G. J.; Fryling, C.; and Delarco, J. E.; "Transforming growth factors produced by certain human tumor cells: polypeptides that interact with epidermal growth factor receptors." PNAS 198077: p 5258–5262
5. Shayab, M.; Plauman, G. D.; McDonald, V. L.; Bradley, J. G.; Todaro, G. J.; "Structure and Function of Human Amphiregulin: A Member of the Epidermal Growth Factor Family" Science 1989, 243, p 1074.
6. Stroobant, P.; Rice, A. P.; Gullick, W. J.; Cheng, D. J.; Kerr, I. M.; Waterfield, M. D.; "Purification and Characterization of Vaccinia Virus Growth Factor." Cell 1985, 42, p 383–393.
7. Proc. R. Soc. Lond [Biol.] Oct. 22, 1985, 226 (1242) p 127–34.
8. Mol All Biol. April 1988 8(4) p 1831–4.
9. EMBO J., 1989, August 13, p 4115–4123).
10. Toneguzzo, F.; Hayclay, A. D.; Keating, A.; 1986 Mol Cell Biol 6. p 703
11. Gluzman, Y., "SV-40 transformed simian cells support the replication of early SV-40 mutants." Cell 1981 23, p 175–182.
12. Maniatis, T.; Fritsch, E. F.; Sambrook, J.; Molecular Cloning: A laboratory manual. 1989 Cold Spring Harbor Laboratory, Cold Spring Harbor, N.Y.
13. Wigler, M.; Perucho, M.; Kurtz, D.; Dana, S.; Pellicer, R.; Axel, R.; Silverstein, S. "Transformation of mammalian cells with an amplifiable dominant acting gene." PNAS 1980, 77, p 3567–3570.
14. U.S. Pat. Nos. 4,745,051 and 4,879,236.
15. Inst. Bio-Organic Chem., Syntex, Res. Palo Alto, Calif. 94304, Proceedings of a Triton BioSciences UCLA Sym., Steamboat Springs, Colo., April 6–13, 1986, XXI, +388p.
16. Nature, (LOND) 318 (6047) 1985. p 663–5.
17. U.S. Pat. No. 4,859,609, issued Aug. 22, 1989 to J. Dull, et al.

I claim:

1. An EGF receptor truncate protein selected from LD$_1$D$_2$D$_3$.ApaL, LD$_2$D$_3$D$_4$ and LD$_3$D$_4$ having EGD binding sites.
2. The protein of claim 1 which is the LD$_1$D$_2$D$_3$.ApaL protein.
3. The protein of claim 1 which is the LD$_2$D$_3$D$_4$ protein.
4. The protein of claim 1 which is the LD$_3$D$_4$ protein.

* * * * *